United States Patent [19]

Tanaka et al.

[11] Patent Number: 4,649,156
[45] Date of Patent: Mar. 10, 1987

[54] 6-NITROPROSTAGLANDIN DERIVATIVES

[75] Inventors: Toshio Tanaka; Atsuo Hazato, both of Hino; Seizi Kurozumi, Kokubunji, all of Japan

[73] Assignee: Teijin Limited, Osaka, Japan

[21] Appl. No.: 756,574

[22] Filed: Jul. 19, 1985

Related U.S. Application Data

[63] Continuation of Ser. No. 525,904, Aug. 24, 1983, abandoned.

[30] Foreign Application Priority Data

| Aug. 24, 1982 | [JP] | Japan | 57-145528 |
| Aug. 24, 1982 | [JP] | Japan | 57-145529 |
| Jun. 13, 1983 | [JP] | Japan | 58-104320 |
| Jun. 30, 1983 | [JP] | Japan | 58-116999 |

[51] Int. Cl.$^4$ .................. A61K 31/215; A61K 31/25; C07C 69/74
[52] U.S. Cl. .................. 514/530; 514/573; 549/214; 549/302; 549/414; 549/415; 549/421; 549/422; 549/473; 549/475; 556/418; 560/21; 560/118; 560/121; 562/435; 562/500; 562/503
[58] Field of Search .................. 560/121, 122, 23, 21, 560/118; 562/503, 504, 434, 435, 500; 556/418; 549/214, 421, 475, 414, 415, 422, 473, 302; 514/530, 573

[56] References Cited

U.S. PATENT DOCUMENTS

| 3,969,396 | 7/1976 | Yankee et al. | 560/121 |
| 4,227,011 | 10/1980 | Chen et al. | 560/121 |
| 4,269,995 | 5/1981 | Sih | 560/121 |

OTHER PUBLICATIONS

Tanaka et al., Tet. Lett., 24 (38), 4103-4 (1983).

Primary Examiner—Nicky Chan
Attorney, Agent, or Firm—Sughrue, Mion, Zinn, Macpeak, and Seas

[57] ABSTRACT

The present invention provides a novel 6-nitroprostaglandin derivatives of the formula (I)

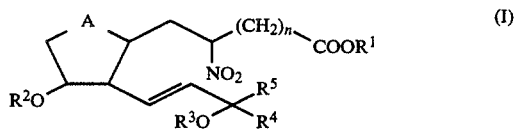

wherein A, n, $R^1$, $R^2$, $R^3$, $R^4$ and $R^5$ are as defined in claim 1.

The 6-nitroprostaglandin derivatives is useful as medicines because of its excellent pharmacological activities including platelet aggregation inhibiting activity, blood pressure lowering activity and anti-ulcerous activity, and useful as intermediate for other pharmaceutically active compounds such as 6-oxoprostaglandin derivatives, prostaglandin $E_1$ derivatives, etc.

14 Claims, No Drawings

6-NITROPROSTAGLANDIN DERIVATIVES

This is continuation of application Ser. No. 525,904, filed 8/24/83, now abandoned.

BACKGROUND OF THE INVENTION

1. Field of the Invention

The present invention relates to novel 6-nitroprostaglandin derivatives, processes for the production thereof, and the use thereof. It is more particularly concerned with novel compounds of 6-nitroplostaglandin derivatives, which are useful as medicines and also useful as intermediates for other medicine because of their pharmacological activities including platelet aggregation inhibiting activity, blood pressure lowering activity, antiulcerous activity, etc., a process for the preparation thereof, and pharmaceutical compositions which contain any of these compounds as active ingredient and a method of preparing other pharmaceutically active compounds by utilizing them.

2. Description of the Prior Art

Natural prostaglandins are known as local hormones having high biological and pharmacological activities and accordingly many research works have been made on their derivatives. Of all such natural prostaglandins, prostaglandin $E_1$ is particularly expected to offer clinical applications because of its strong platelet aggregation inhibiting activity and vasodilating activity.

Of recent years 6-oxoprostaglandin $E_1$, which is deemed to be a derivative of prostaglandin $E_1$, has been discovered as a biological active metabolite of prostacyclin. 6-Oxoprostaglandin $E_1$ has strong platelet aggregation inhibiting activity and blood pressure lowering activity resulting from smooth muscle dilating function same as prostacyclin and is expected to have uses in the ingredient of pharmaceutical compositions (European Journal of Pharmacology, Vol. 57, p. 273 (1979); ibid. Vol. 60, p. 245 (1979)). Studies have also been made on various derivatives of 6-oxoprostaglandin $E_1$ (Japanese Laid-Open Patent Publication No. 44639/79) and furthermore researches on 6-hydroxyprostaglandin $E_1$ and its derivatives derived from 6-oxoprostaglandin $E_1$ and its derivatives have been conducted (U.S. Pat. No. 4,131,738).

Also, 6-oxoprostaglandin $F_1\alpha$ is known as a metabolite of prostacyclin (Biochem. Biophys. Acta., 574, 182 (1979)). Though 6-oxoprostaglandin $F_1\alpha$ is an inactive metabolite, it is expected to be used as a diagnosticum for determining the concentration of prostacyclin in the blood (Brit. J. of Urology, 54, 26 (1982)).

SUMMARY OF THE INVENTION

As the result of an elaborate study aiming at the introduction of a functional group at the 6-position of prostaglandin $E_1$ or prostaglandin $F_1$, the inventors of the present invention have succeeded in preparing novel 6-nitroprostaglandin derivatives having a nitro group introduced at their 6-positions with the accompaniment of findings that these 6-nitroprostaglandin derivatives are useful as medicine because of their excellent pharmacological activities such as platelet aggregation inhibiting activity, blood pressure lowering activity, and antiulcerous activity, and that they are useful compounds which can be used as intermediates for the preparation of 6-oxoprostaglandins $E_1$, prostaglandins $E_1$, prostaglandins $F_1$, or prostacyclins, thus completing the present invention.

The present invention relates to a 6-nitroprostaglandin derivatives of the following formula (I)

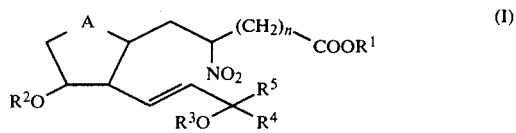

wherein A represents a carbonyl group or a hydroxylmethylene group, n represents an integer of to 1 to 4, $R^1$ represents a hydrogen atom, a $C_1$–$C_{10}$ alkyl group, a substituted or unsubstituted phenyl group, a substituted or unsubstituted alicyclic group, a substituted or unsubstituted phenyl ($C_1$–$C_2$) alkyl group, or one equivalent of cation; $R^2$ and $R^3$ are indentical or different and each represents a hydrogen atom, a tri ($C_1$–$C_7$) hydrocarbonsilyl group, or a group forming an acetal linkage together with the oxygen atom of the hydroxyl group; $R^4$ represents a hydrogen atom, a methyl group, a ethyl group, a vinyl group, or an ethynyl group; and $R^5$ represents an unsubstituted $C_5$–$C_8$ alkyl group, a substituted $C_1$–$C_5$ alkyl group substituted by a substituent selected from phenyl, phenoxy, $C_1$–$C_6$ alkoxy and $C_5$–$C_6$ cycloalkyl, which substituent may be substituted, or a substituted or unsubstituted alicyclic group. Since the 6-nitroprostaglandin derivatives of this invention have outstanding pharmacological activities such as platelet aggregation inhibiting activity, blood pressure lowering activity, antiulcerous activity, etc., they can be administered to subjected for vasodilation, blood pressure lowering or antithrombosis and also for controlling various conditions such as angina pectoris, arteriosclerosis, myocardial infarction, endotoxin shock, pulmonary hypertension, cerebral apoplexy, transient ischemic attack, thrombocytopenic purpura, deep vein thrombosis and peripheral vascular diseases. The active compound of this invention can be administered for inhibiting metastatis of malignant tumors.

Especially the 6-nitroprostaglandin $E_1$ derivatives have better selective biological activity than natural prostaglandin $E_1$.

Furthermore, the 6-nitroprostaglandin derivatives of the present invention can be easily converted into prostaglandins $E_1$ and 6-oxoprostaglandines $E_1$, which are both useful as medicine, or 6-oxoprostaglandins $F_1$, which is useful as a diagnosticum, and accordingly they are useful as the intermediates for the preparation of other medicine or diagnosticums.

DESCRIPTION ON THE PREFERRED EMBODIMENTS

The 6-nitroprostaglandin derivatives of the present invention is expressed by the aforementioned formula (I).

In the formula (I) A represents a carbonyl group or a hydroxylmethylene group. For the sake of convenience, the 6-nitroprostaglandin derivative of this invention can be divided into the following two groups according to the definition of A.

(1) 6-nitroprostaglandin $E_1$ derivatives of formula (1)-a

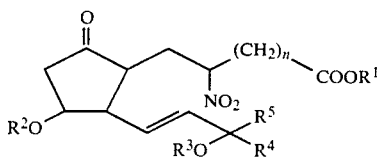

wherein all symbols are as defined with regard to formula (1):

(2) 6-nitroprostaglandin $F_1$ derivatives of formula (1)-b

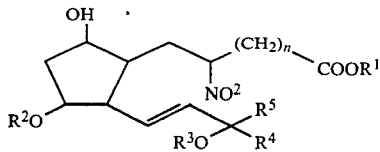

wherein all symbols are as defined with regard to formula (1).

In the formula (1) n represents an interger of 1 to 4.

In the formula (1) $R^1$ represents a hydrogen atom, a $C_1-C_{10}$ alkyl group, a substituted or unsubstituted phenyl group, a substituted or unsubstituted alicyclic group, a substituted or unsubstituted phenyl ($C_1-C_2$) alkyl group, or one equivalent of cation.

The $C_1-C_{10}$ alkyl group are linear or branched alkyl groups having 1 to 10 carbon atoms such as methyl, ethyl, n-propyl, iso-propyl, n-butyl, sec-butyl, tert-butyl, n-pentyl, n-hexyl, n-heptyl, n-octyl, n-nonyl and n-decyl.

Preferred substituents for the substituted phenyl group are a halogen atom, a hydroxyl group, a $C_2-C_7$ acyloxy group, a $C_1-C_4$ alkyl group which may be substituted by a halogen atom, a $C_1-C_4$ alkyl group which may be substituted by a halogen atom, a $C_1-C_4$ alkoxy group which may be substituted by a halogen atom, a nitrile group, a carboxyl group, or a ($C_1-C_6$) alkoxycarbonyl group. The halogen atom includes fluorine, chlorine and bromine, the fluorine and chlorine being preferred. Examples of the $C_2-C_7$ acyloxy group are acetoxy, propionyloxy, n-butyryloxy, iso-butyryloxy, n-valeryloxy, iso-valeryloxy, caproyloxy, enanthoyloxy and benzoyloxy. Examples of the $C_1-C_4$ alkyl group which may be substituted by one or more halogen atoms are methyl, ethyl, n-propyl, iso-propyl, n-butyl, chloromethyl, dichloromethyl, and trifluoromethyl. Preferred examples of the $C_1-C_4$ alkoxy group which may be substituted by one or more halogen atoms are methoxy, ethoxy, n-propoxy, iso-propoxy, n-butoxy, chloromethoxy, dichloromethoxy and trifluoromethoxy. Examples of the ($C_1-C_6$) alkoxycarbonyl group include methoxycarbonyl, ethoxycarbonyl, butoxycarbonyl and hexyloxycarbonyl.

The substituted phenyl group may have 1 to 3, preferably 1, such substituents as exemplified above.

The substituted or unsubstituted alicyclic group includes, for example, saturated or unsaturated $C_5-C_8$, preferably $C_5-C_6$, especially preferably $C_6$, alicyclic groups which are unsubstituted or substituted by the same substituents as exemplified hereinabove, such as cyclopentyl, cyclohexyl, cyclohexenyl, cycloheptyl, and cyclooctyl.

Examples of the substituted or unsubstituted phenyl ($C_1-C_2$) alkyl group are benzyl, α-phenethyl and β-phenethyl in which the phenyl group is unsubstituted or substituted by the same substitutes as exemplified hereinabove.

Examples of one equivalent of cation are ammonium cations such as $NH_4^+$, tetramethylammonium monomethylammonium, dimethylammonium, trimethylammonium, benzylammonium, phenethylammonium, morpholium cation monoethanolammonium, and piperidium cation; alkali metal cations such as $Na^+$ and $K^+$; and divalent or trivalent metallic metallic cations such as $\frac{1}{2}Ca^{2+}$, $\frac{1}{2}Mg^{2+}$, $\frac{1}{2}Zn^{2+}$, and $\frac{1}{3}Al^{3+}$.

$R^1$ is preferably a hydrogen atom, a $C_1-C_{10}$ alkyl group, or one equivalent of a cation.

In the formula (I) $R^2$ and $R^3$ are identical or different, and each represents a hydrogen atom, a tri($C_1-C_7$)hydrocarbon-silyl group or a group forming an acetal linkage together with the oxygen atom of the hydroxyl group. Examples of the tri($C_1-C_7$)hydrocarbon-silyl group are tri($C_1-C_4$) alkylsilyl groups such as trimethylsilyl, triethylsilyl, and t-butyldimethylsilyl, diphenyl ($C_1-C_4$) alkylsilyl groups such as t-butyldiphenylsilyl, and a tribenzylsilyl group.

Examples of the group forming an acetal linkage together with the oxygen atom of the hydroxyl group are methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxo-bicyclo[3.1.0] hex-4-yl. Of these, 2-tetrahydropyranyl, 2-tetrahydrofuranyl, 1-ethoxyethyl, 2-methoxy-2-propyl, (2-methoxyethoxy)methyl, and 6,6-dimethyl-3-oxa-2-oxo-bicyclo[3.1.0]hex-4-yl are preferred.

It should be understood that these hydrocarbonsilyl groups and acetal linkage-forming groups are protective groups for the hydroxyl group. These protective groups can be easily removed under acidic to neutral conditions.

Preferred as $R^2$ or $R^3$ are a hydrogen atom, a tri($C_1-C_4$)alkylsilyl group, a diphenyl ($C_1-C_4$) alkylsilyl group, a 2-tetrahydropyranyl group, a 2-tetrahydrofuranyl group, a 1-ethoxyethyl group, a 2-methoxy-2-propyl group, a (2-methoxyethoxy)methyl group, or a 6,6-dimethyl-3-oxa-2-oxo-bicyclo[3.1.0] hexy-4-yl group.

In the formula (I) $R^4$ represent a hydrogen atom, a methyl group, a ethyl group, a vinyl group, or an ethynyl group, the hydrogen atom and the methyl group being preferred.

In the formula (I) $R^5$ represents unsubstituted $C_5-C_8$ alkyl group; a substituted $C_1-C_5$ alkyl group substituted by a substituent selected from a phenyl group, a phenoxy group, a $C_1-C_6$ alkoxy group and a $C_5-C_6$ cycloalkyl group, which substituent may be substituted; or a substituted or unsubstituted alicyclic group. The unsubstituted $C_5-C_8$ alkyl group may be linear or branched, and includes, for example, n-pentyl, n-hexyl, 2-methyl-1-hexyl, 2-methyl-2-hexyl, n-heptyl, and n-octyl. The n-pentyl, n-hexyl, 2-methyl-1-hexyl, and 2-methyl-2-hexyl are preferred. The substituted $C_1-C_5$ alkyl group may be linear or branched, and includes, for example, methyl, ethyl, n-propyl, iso-propyl, n-butyl, sec-butyl, t-butyl and n-pentyl. These alkyl groups are substituted by a phenyl group; a phenoxy group; a $C_1-C_6$ alkoxy group such as methoxy, ethoxy, n-propoxy, iso-propoxy, n-butoxy, iso-butoxy, t-butoxy, n-pentoxy, or n-hexoxy; or a $C_5-C_6$ cycloalkyl group such as cyclopentyl or cyclohexyl. These substituents may be substituted by the same substitutents as cited hereinabove as the substituents for the substituted phenyl group $R^1$.

Examples of preferred substituted $C_1$–$C_5$ alkyl groups are $C_1$–$C_2$ alkyl groups substituted by a phenoxy or phenyl group which may be further be substituted by a chlorine or fluorine atom or a methyl, ethyl or trifluoro methyl group; and propoxymethyl, ethoxyethyl, propoxyethyl, butoxymethyl, methoxymethyl, ethoxyethyl, propoxyethyl, butoxymethyl, methoxypropyl, 2-ethoxy-1,1-dimethylethyl, propoxydimethylmethyl, cyclohexylmethyl, cyclohexylethyl, cyclohexyldimethylmethyl and 2-cyclohexyl-1,1-dimethyl-ethyl. The substituted or unsubstituted alicyclic group may include the same species as cited with regard to $R^1$.

The 6-nitroprostaglandin derivatives expressed by the formula (I) of the present invention contain asymmetric carbon atoms in their molecules and the present invention involves all the stereoisomers and optical isomers, which arise from these asymmetric carbon atoms, and mixtures thereof.

Of all these isomers, natural-type 6-nitroprostaglandin derivatives expressed by the following formula (I)-a-1

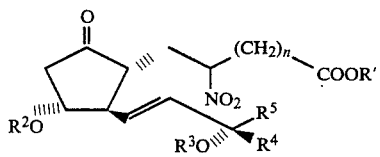

wherein all symbols are as defined with regard to formula (I),
or natural-type 6-nitroprostaglandin $F_{1\alpha}$ derivatives expressed by the following formula (I)-b-1

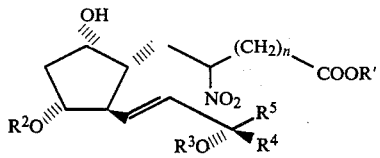

wherein all symbols are as defined with regard to formula (I),
are preferable.

The present invention also involves various isomers other than those mentioned above and an explanation is given below taking the 6-nitroprostaglandin $E_1$ derivatives of formula (I)-a by way of example.

As the 15-epimers of natural-type 6-intropostaglandin $E_1$ derivatives of formula (I)-a-1, compounds expressed by the following formula (I)a-2 may be mentioned

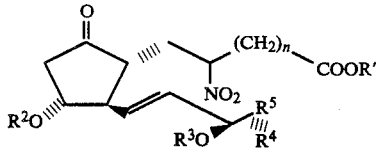

wherein all symbols are as defined with regard to formula (I).
These compounds differ from the compounds of formula (I)-a-1 in regard to the configuration of the asymmetric carbon atom at the 15-position.

As the enantomers of the compounds of formula (I)-a-1 or formula (I)-a-2, there are compounds expressed by the following formula (I)-a-1-ent

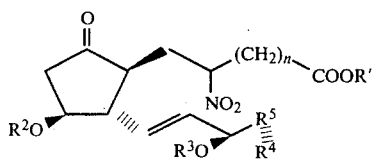

or by the following formula (I)-a-2-ent

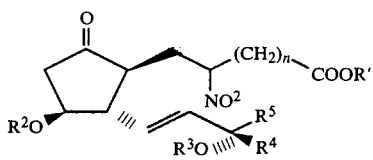

wherein all symbols are as defined with regard to formula (I).

The compounds of formula (I)-a-1-ent or formula (I)-a-2-ent differ from the compounds of formula (I) in regard to the configurations of the asymmetric carbon atoms at the 18-, 11-, and 15-positions.

(i) Specific examples of the 6-nitroprostaglandin $E_1$ derivatives of formula (I)-a are given below.

| | |
|---|---|
| (100) | 6-nitroprostaglandin $E_1$ |
| (102) | 15-methyl-6-nitroprostaglandin $E_1$ |
| (104) | 16-methyl-6-nitroprostaglandin $E_1$ |
| (106) | 17-methyl-6-nitroprostaglandin $E_1$ |
| (108) | 18-methyl-6-nitroprostaglandin $E_1$ |
| (110) | 19-methyl-6-nitroprostaglandin $E_1$ |
| (112) | 20-methyl-6-nitroprostaglandin $E_1$ |
| (114) | 20-ethyl-6-nitroprostaglandin $E_1$ |
| (116) | 20-propyl-6-nitroprostaglandin $E_1$ |
| (118) | 16-ethyl-6-nitroprostaglandin $E_1$ |
| (120) | 17-ethyl-6-nitroprostaglandin $E_1$ |
| (122) | 15,16-dimethyl-6-nitroprostaglandin $E_1$ |
| (124) | 16,17-dimethyl-6-nitroprostaglandin $E_1$ |
| (126) | 16,20-dimethyl-6-nitroprostaglandin $E_1$ |
| (128) | 17,20-dimethyl-6-nitroprostaglandin $E_1$ |
| (130) | 16,16,20-trimethyl-6-nitroprostaglandin $E_1$ |
| (132) | 17-methyl-20-ethyl-6-nitroprostaglandin $E_1$ |
| (134) | 15-cyclopentyl-w-pentanor-6-nitroproslagtandin $E_1$ |
| (136) | 15-cyclohexyl-w-pentanor-6-nitroprostaglandin $E_1$ |
| (138) | 15-(2,3-diethyl)cyclopentyl-w-pentanor-6-nitroprostaglandin $E_1$ |
| (140) | 15-(4-t-butyl)cyclohexyl-w-pentanor-6-nitroprostaglandin $E_1$ |
| (142) | 16-cyclopentyl-w-tetranor-6-nitroprostaglandin $E_1$ |
| (144) | 16-cyclohexyl-w-tetranor-6-nitroprostaglandin $E_1$ |
| (146) | 17-cyclopentyl-w-trinor-6-nitroprostaglandin $E_1$ |
| (148) | 18-cyclohexyl-w-dinor-6-nitroprostaglandin $E_1$ |
| (150) | 19-cyclopentyl-w-nor-6-nitroprostaglandin $E_1$ |
| (152) | 18-oxa-6-nitroprostaglandin $E_1$ |
| (154) | 17-oxa-6-nitroprostaglandin $E_1$ |
| (156) | 16-phenyl-w-tetranor-6-nitroprostaglandin $E_1$ |
| (158) | 17-phenyl-w-trinor-6-nitroprostaglandin $E_1$ |
| (160) | 16-(p-chlorophenyl)-w-tetranor-6-nitroprostaglandin $E_1$ |
| (162) | 17-(m-trifluromethylphenyl)-w-trinor-6-nitroprostaglandin $E_1$ |
| (164) | 16-(p-methylphenyl)-w-tetranor-6-nitroprostaglandin $E_1$ |
| (166) | 16-phenoxy-w-tetranor-6-nitroprostaglandin $E_1$ |
| (168) | 16-(m-fluorophenoxy)-w-tetranor-6-nitroprostaglandin $E_1$ |
| (170) | 16-(p-fluorophenoxy)-w-tetranor-6-nitroprostaglandin $E_1$ |

| | -continued |
|---|---|
| (172) | methyl ester of (100) |
| (174) | methyl ester of (102) |
| (176) | methyl ester of (104) |
| (178) | methyl ester of (128) |
| (180) | methyl ester of (134) |
| (182) | methyl ester of (136) |
| (184) | methyl ester of (156) |
| (186) | ethyl ester of (100) |
| (188) | ethyl ester of (160) |
| (190) | n-butyl ester of (102) |
| (192) | n-propyl ester of (142) |
| (194) | n-hexyl ester of (134) |
| (196) | n-decyl ester of (158) |
| (198) | sodium salt of (102) |
| (200) | sodium salt of (128) |
| (202) | sodium salt of (130) |
| (204) | sodium salt of (168) |
| (206) | 11,15-bis(t-butyldimethylsilyl)ester of (120) |
| (208) | 11,15-bis(t-butyldimethylsilyl)ester of (138) |
| (210) | 11,15-bis(t-butyldimethylsilyl)ester of (140) |
| (212) | 2,3-dinor-6-nitroprostaglandin $E_1$ |
| (214) | 15-methyl-2,3-dinor-6-nitroprostaglandin $E_1$ |
| (216) | 16-methyl-2,3-dinor-6-nitroprostaglandin $E_1$ |
| (218) | 19-methyl-2,3-dinor-6-nitroprostaglandin $E_1$ |
| (220) | 20-ethyl-2,3-dinor-6-nitroprostaglandin $E_1$ |
| (222) | 16-ethyl-2,3-dinor-6-nitroprostaglandin $E_1$ |
| (224) | 17,20-dimethyl-2,3-dinor-6-nitroprostaglandin $E_1$ |
| (226) | 15,16-dimethyl-2,3-dinor-6-nitroprostaglandin $E_1$ |
| (228) | 2,3-dinor-15-cyclopentyl-w-pentanor-6-nitro-prostaglandin $E_1$ |
| (230) | 2,3-dinor-15-cyclohexyl-w-pentanor-6-nitroprostaglandin $E_1$ |
| (232) | 2,3-dinor-16-cyclohexyl-w-tetranor-6-nitroprostablandin $E_1$ |
| (234) | 18-oxa-2,3-dinor-6-nitroprostaglandin $E_1$ |
| (236) | 2,3-dinor-16-phenyl-w-tetranor-6-nitro-prostaglandin $E_1$ |
| (238) | 2,3-dinor-17-phenyl-w-trinor-6-nitro-prostaglandin $E_1$ |
| (240) | methyl ester of (212) |
| (242) | methyl ester of (214) |
| (244) | ethyl ester of (216) |
| (246) | ethyl ester of (218) |
| (248) | propyl ester of (220) |
| (250) | sodium salt of (220) |
| (252) | sodium salt of (222) |
| (254) | 11,15-bis(t-butyldimethylsilyl)ester of (224) |
| (256) | 11,15-bis(t-butyldimethylsilyl)ester of (226) |
| (258) | 11,15-bis(t-butyldimethylsilyl)ester of (228) |

(ii) Specific examples of the 6-nitroprostaglandin $E_1$ derivatives of formula (I)-b are given below.

| | |
|---|---|
| (300) | 6-nitroprostaglandin $F_{1\alpha}$ |
| (302) | 15-methyl-6-nitroprostablandin $F_{1\alpha}$ |
| (304) | 16-methyl-6-nitroprostaglandin $F_{1\alpha}$ |
| (306) | 17-methyl-6-nitroprostaglandin $F_{1\alpha}$ |
| (308) | 18-methyl-6-nitroprostaglandin $F_{1\alpha}$ |
| (310) | 19-methyl-6-nitroprostaglandin $F_{1\alpha}$ |
| (312) | 20-ethyl-6-nitroprostaglandin $F_{1\alpha}$ |
| (314) | 16-ethyl-6-nitroprostaglandin $F_{1\alpha}$ |
| (316) | 17-ethyl-6-nitroprostaglandin $F_{1\alpha}$ |
| (318) | 15,16-dimethyl-6-nitroprostaglandin $F_{1\alpha}$ |
| (320) | 17,20-dimethyl-6-nitroprostaglandin $F_{1\alpha}$ |
| (322) | 17-methyl-20-ethyl-6-nitroprostaglandin $F_{1\alpha}$ |
| (314) | 15-cyclopentyl-w-pentanor-6-nitroprostagrandin $F_{1\alpha}$ |
| (316) | 15-cyclohexyl-w-pentanor-6-nitroprostaglandin $F_{1\alpha}$ |
| (318) | 16-cyclopentyl-w-tetranor-6-nitroprostaglandin $F_{1\alpha}$ |
| (320) | 16-cyclohexyl-w-tetranor-6-nitroprostaglandin $F_{1\alpha}$ |
| (322) | 17-cyclopentyl-w-trinor-6-nitroprostaglandin $F_{1\alpha}$ |
| (324) | 19-cyclopentyl-w-nor-6-nitroprostaglandin $F_{1\alpha}$ |
| (326) | 18-oxa-6-nitroprostaglandin $F_{1\alpha}$ |
| (328) | 16-phenyl-w-tetranor-6-nitroprostagrandin $F_{1\alpha}$ |

| | -continued |
|---|---|
| (330) | 16-(m-fluorophenoxy)-w-tetranor-6-nitro-prostaglandin $F_{1\alpha}$ |
| (332) | 2,3-dinor-6-nitroprostaglandin $F_{1\alpha}$ |
| (334) | 15-methyl-2,3-dinor-6-nitroprostaglandin $F_{1\alpha}$ |
| (336) | 17,20-dimethyl-2,3-dinor-6-nitroprostaglandin $F_{1\alpha}$ |
| (338) | methyl ester of (300) |
| (340) | methyl ester of (302) |
| (342) | methyl ester of (304) |
| (344) | ethyl ester of (306) |
| (346) | propyl ester of (308) |
| (348) | sodium salt of (310) |
| (350) | sodium salt of (312) |
| (352) | sodium salt of (314) |
| (354) | 11,15-bis(t-butyldimethylsilyl)ether of (316) |
| (356) | 11,15-bis(t-butyldimethylsilyl)ether of (318) |
| (358) | 11,15-bis(t-butyldimethylsilyl)ether of (320) |
| (360) | their isomers of (300)-(358) |

All of the above-exemplified compounds are natural-type 6-nitroprostaglandin $E_1$ derivatives of 6-nitroprostaglandin $F_{1\alpha}$ derivatives. The corresponding 15-epimers of these 6-nitroprostaglandin $E_1$ or $F_{1\alpha}$ derivatives and the corresponding enantimers of these may also be cited as examples.

The 6-nitroprostaglandin $E_1$ derivatives of the following formula (I)-a

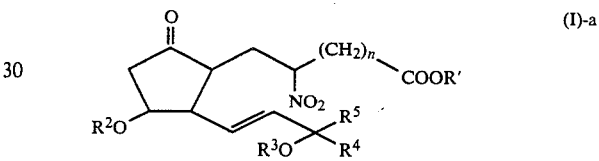

wherein n, $R^1$, $R^2$, $R^3$, $R^4$ and $R^5$ are as defined with regard to formula (I), are produced in accordance with this invention by reacting a 4-substituted-2-cyclopentenone of the following formula (II)

wherein $R^{21}$ represents a tri($C_1$-$C_7$)hydroxarbonsilyl group, or a group forming an acetal linkage together with the oxygen atom of the hydroxyl group,
with an organocupper reagent resulting from an organolithium compound of the formula (III-1)

wherein $R^5$ is as defined above, $R^{31}$ represents a tri($C_1$-$C_7$)hydrocarbon-silyl group or a group forming an acetal linkage together with the oxygen atom of the hydroxyl group, $R^{41}$ represents a hydrogen atom, a methyl group, a ethyl group, a vinyl group, or a protected ethynyl group,
and a cuprous salt of the formula (III-2)

$$CuQ \qquad (III-2)$$

wherein Q represents a halogen atom, a $C_1$-$C_6$ alkoxy group, a phenoxy group, a phenylthio group, a di(C-

$_1$-C$_6$)alkylamino group, a C$_1$-C$_5$ alkyl-substituted ethynyl group or cyano group,
in the presence of an aprotic inert organic solvent to effect conjugation addition reaction and followed with the reaction with a nitroolefin compound of the formula (IV)

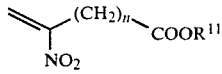  (IV)

wherein n represents an integer of 1 to 4, R$^{11}$ represents a C$_1$-C$_{10}$ alkyl group, a substituted or unsubstituted phenyl group, a substituted or unsubstituted alicyclic group, or a substituted or unsubstituted phenyl (C$_1$-C$_2$) alkyl group,
and thereafter, if required, subjecting the reacting product to a reaction of removing the protective group and/or a hydrolysis reaction and/or a salt-forming reaction.

The 4-substituted-2-cyclopentenone of formula (II) are compounds which do not contain active hydrogen atom as is seen from the definitions of R$^{21}$ in formula (II). The definitions of R$^{21}$ differ from the definitions of R$^2$ in formula (I) only in that formula (II) show compounds free of active hydrogen. Specific examples of R$^{21}$ are therefore evident from the foregoing description. The 4-substituted-2-cyclopentenone can be produced in accordance with the process described in Tetrahedron. Vol. 32, pp. 1713 to 1718. (1976).

In general formula (III-1) representing the organolithium compound to obtain the organocupper reagent used as the starting material in the process of this invention, R$^5$ is defined with regard to formula (I). R$^{31}$ is a tri(C$_1$-C$_7$) hydrocarbonsilyl group or a group forming an acetal linkage together with the oxygen atom of hydroxyl group. Specific examples of R$^5$ and R$^{31}$ are evident from the foregoing description. R$^{41}$ represents a hydrogen atom, a methyl group, a ethyl group, a vinyl group, or a protected ethylnyl group such as trimethylsilylethynyl or t-butyldimethylsilyl ethynyl. In general formula (III-2) representing the cuprous salt, Q represents a halogen atom such as chlorine, bromine, or iodine; a C$_1$-C$_6$ alkoxy group such as methoxy, ethoxy, n-propoxy, iso-propoxy, n-butoxy, n-pentoxy, or n-hexoxy; a phenoxy group; a phenylthio group; a (C$_1$-C$_6$)alkylamino group such as dimethylamino, diethylamino or dihexylamino; a C$_1$-C$_5$ alkylsubstituted ethynyl group such as methylethynyl, propylethynyl, t-butylethynyl or pentylethynyl; or a cyano group.

The organocupper reagent can be produced by reacting the organolithum compound with the cuprous salt (see, for example, Organic Reaction, Vol. 19, p. 19 (1972), Tetrahedron Lett., 21, 1247 (1980)). The organolithium compound is used in an amount of usually about 0.8 to about 3 moles, preferably 1 to 2 moles, per mole of the cuprous salt.

Another starting material compounds, nitroolefin compounds expressed by formula (IV), to be used in the process of the present invention are compounds which do not contain an active hydrogen atom and one equivalent of cation as is seen from the definition of R" in formula (IV). Specific examples of R" are therefore evident from the foregoing description.

The abovementioned nitroolefin compounds are compounds which can be obtained with comparative ease since they can be prepared according to the ordinary methods of preparing nitroolefin. For instance, the Journal of the American Chemical Society, Vol. 98, 4679 (1976) and the literature cited therein may be helpful in obtaining hints on such methods, which can be summarized schematically as follows:

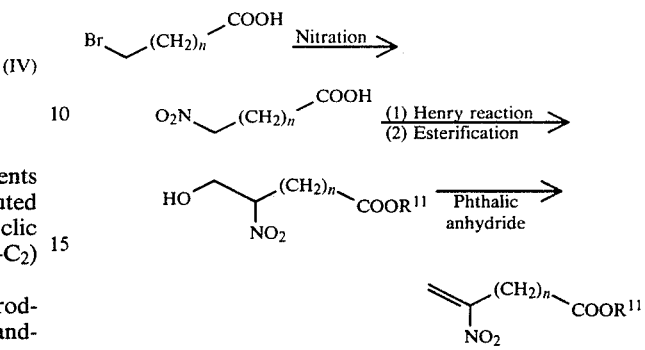

wherein n and R$^{11}$ are defined above.

The process of the present invention is initiated with the reaction of the 4-substituted-2-cyclopentenone expressed by said formula (II) with an organocupper reagent resulting from a organolithum compound expressed by said formula (III-1) and a cuprous salt of the formula (III-2) in the presence of an aprotic inert organic solvent.

Stoichiometrically, said 4-substituted-2-cyclopentenone and said organocupper reagent react in equimolar proportions. Usually, 0.5 to 2.0 moles, preferably 1.5 moles, of the organocupper reagent is used per mole of the 4-substituted-2-cyclopentenone.

The reaction temperature is from $-120°$ C. to $0°$ C., preferably from $-90°$ C. to $-30°$ C. The reaction time varies depending upon the reaction temperature; however, the reaction conducted for about one hour at $-78°$ C. to $-20°$ C. is usually enough to obtain a desired result.

The reaction is carried out in the presence of an organic solvent. An aprotic inert organic solvent which remains liquefied in the reaction temperature and does not react with the reacting species is used.

As the aprotic inert organic solvents, there are, for instance, such saturated hydrocarbons as pentane, hexane, and heptane, such aromatic hydrocarbons as benzene, toluene, and xylene, such ethereal solvents as diethyl ether, tetrahydrofuran, dioxane, dimethoxyethane, and diethylene glycol dimethyl ether, and other aprotic polar solvents such as hexamethyl phosphoric triamide (HMP), N,N-dimethylformamide (DMF), N,N-dimethylacetamide (DMAC), dimethyl sulfoxide, sulfolane, and N-methylpyrrolidone may be mentioned and they can be used as a mixed solvent consisting of more than one. The inert solvent which is used in the preparation of an organocupper reagent can also be used as said aprotic inert organic solvent. In this case, said initial reaction can be carried out effectively by adding said 4-substituted-2-cyclopentenone to the reaction system in which the preparation of the organocupper reagent has been completed. Said organic solvents may be used in an amount that is enough to allow the reaction to proceed satisfactorily and they are usually used 1 to 100 times the material by volume, preferably 2 to 30 times the material by volume.

Desirably, the reaction is carried out in an atomosphere of an inert gas such as nitrogen or organ.

Preferably, the reaction is carried out in the presence of a trivalent phosphorus compound. The trivalent phosphorus compound serves to dissolve the organocupper reagent uniformly in the aprotic inert organic solvent and to cause the reaction to proceed smoothly. Hence, the trivalent phosphorus compound may also be caused to be present during the preparation of the organocupper reagent, and the 4-substituted-2-cyclopentenone may be added to the reaction mixture of the organocupper reagent to carry out the reaction there.

Exemplary of the trivalent phosphorus compound are such $tri(C_1-C_6)$alkylphosphines as trimethylphosphine, triethylphosphine, tri-n-butylphosphine and tri-n-hexylphosphine, such $tri(C_1-C_6)$alkylphosphites as trimethylphosphites, triethylphosphites, isopropyl phosphites, tri-n-butylphosphite and tri-n-hexylphosphite, and also hexamethylphosphorus triamide.

In devising the process of the present invention it is assumed that, through the preceding procedure of making the 4-substituted-2-cyclopentenone react with the organocupper reagent, an alkenyl group which forms the organic group of said organocupper reagent is introduced to the 3-position of said 4-substituted-2-cyclopentenone and a conjugated enolate arising from anions is formed at the 2-position. In the process of the present invention, the desired 6-nitroprostaglandin $E_1$ derivatives can be obtained by making said nitroolefin compounds expressed by formula (IV) react with this conjugated enolate. The reaction of nitroolefin compounds can be effected by introducing a nitroolegin compound expressed by said formula (IV), which may be diluted by said aprotic inert organic solvent, into the reaction system in which an organocupper reagent is made to conjugate with a 4-substituted-2-cyclopentenone.

Said nitroolefin compounds are made to react with enolate formed by conjugation addition is equimolar proportions stoichiometrically; however, it is an ordinary practice to use 0.5 to 2.0 moles, preferably 0.8 to 1.2 moles, of them per mole of the initially used 4-substituted-2-cyclopentenone.

The reaction temperature is approximately in the range of $-120°$ C. to $0°$ C., preferably in the range of $-90°$ C. to $-30°$ C. The reaction time varies depending upon the reaction temperature; however, the reaction conducted for about one hour at $-78°$ C. to $-40°$ C. is usually enough to obtain a desired result. It is efficient to trace the reaction and determine its termination by thin layer chromatography, etc.

After the reaction is over, the obtained product is separated from the reaction mixture and purified according to the ordinary methods such as extraction, washing, and chromatography or the combination thereof.

Out of those compounds expressed by said formula (I), the 6-nitroprostaglandin $E_1$ ester derivatives with protected hydroxyl groups are thus obtained. Thereafter, the protective group for the hydroxyl group is made into a free hydroxyl group according to the ordinary method, and/or the hydroxyl group in the form of an ester is hydrolyzed according to the ordinary method, and/or they are subjected to the salt-forming reaction, thus producing the 6-nitroprostaglandin $E_1$ derivatives of the present invention.

When the protective group ($R^{21}$ and/or $R^{31}$) for the hydroxyl group is a group forming an acetal linkage together with the oxygen atom of the hydroxyl group, the deprotecting reaction is conveniently carried out in water, tetrahydrofuran, diethylether, dioxane, acetone, acetonitrite etc. as a reaction solvent using acetic acid, a pyridinium salt of p-toluenesulfonic acid, cation-exchange resin, etc. as a catalyst. The reaction is carried out at a temperature in the range of from $-78°$ C. to $+100°$ C. for about 10 minutes to about 3 days. When the protective group is a $tri(C_1-C_7)$hydrocarbon-silyl group, the deprotecting reaction is carried out at the same for the same period of time as described above in the same reaction solvent as described above in the presensence of acetic acid, hydrofluoric acid, tetrabutyl ammonium fluoride, cesium fluoride, etc. The hydrolysis of the ester group ($R^{11}$) is carried out by using an enzyme such as esterase lipase in water or a water-containing solvent at a temperature of from $-10°$ C. to $+100°$ C. for a period of from about 10 minutes to about 24 hours. The compound having a carboxyl group resulting from the above deprotecting reaction to form the corresponding carboxylate salt. The salt-forming reaction is known per se, and can be carried out by neutralizing the carboxylic acid with a nearly equivalent amount of a basic compound such as sodium hydroxide, potassium hydroxide, sodium carbonate, ammonia, trimethylamine, monoethanolamine, or morpholine in a usual manner.

The conjugation addition reaction in accorance with this invention proceeds stereospecifically. This means that the configuration of the substituent-$OR^{21}$ at the 4-position of the 4-substituted-2-cyclopentenone of formula (II) determines the direction in which the group

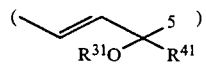

from the organocupper reagent produced from the organolithum compound of formula (III-1) and the cuprous salt of formula (III-2) is introduced into the skelton of the cyclopentenone.

Accordingly, when

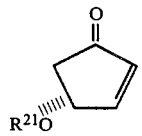

and the organocupper reagent resulting from the organolithum compound of the following formula (III-1')

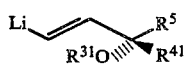 (III-1')

and the cuprous salt of formula (III-2) are subjected to conjugation addition reaction, only a natural-type 6-nitroprostaglanding $E_1$ derivatives of the following formula (I)-a-1 is formed.

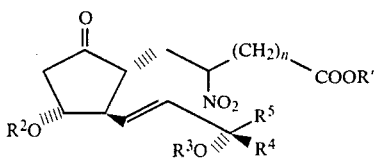

(I)-a-1

Similarly, when a compound of the following formula

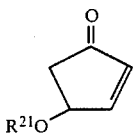

and the same organocupper reagent as above are subjected to conjugation addition reaction, a 15-epi enantiomer (diastereomer) alone of the above natural-type 6-nitroprostaglandin $E_1$ derivatives which is expressed by the following formula (I)-a-2-ent results.

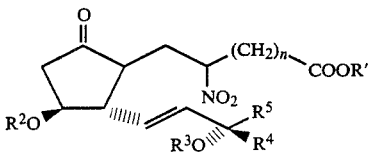

(I)-a-2-ent when a compound of the following formula

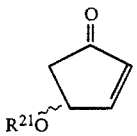

wherein ~ means a mixed bond of ||||| and ⎯⎯,
and the same organocupper reagent are subjected to conjugation addition reaction, a mixture of the compound of formula (I)-a-1 and (I)-a-2-ent is formed.

The 6-nitroprostaglandin $F_1$ derivatives of the following formula

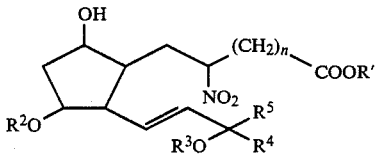

(I)-b wherein n, $R^1$, $R^2$, $R^3$, $R^4$ and $R^5$ are as defined with regard to formula (I),
are produced in accordance with this invention by reducing the 6-nitroprostaglandin $E_1$ derivatives of the fomula (I)-a, and, if required, subjecting the reduction product to a reaction of removing the protective group and/or a hydrolysis reaction and/or a salt-forming reaction.

As the reducing agents to be used in said reduction reaction, such borohydride metallic compounds as sodium borohydride, lithium borohydride, potassium borohydride, zinc borohydride, lithium hydride trialkyl $(C_1 \sim C_4)$ boran, potassium hydride trialkyl $(C_1 \sim C_4)$ boran, etc. and such aluminum compounds as diisobutyl aluminum hydride, diisobutyl aluminum-2,6-di-t-butyl-4-methylphenoxide, etc. may be mentioned.

As the solvents to be used in the reduction reaction, such alcohols as methanol, ethanol, propanol, etc., such ethers as diethylether, tetrahydrofuran, dioxane etc. and such hydrocarbons as benzene, toluene, hexane, heptane etc. may be mentioned.

The above-mentioned reducing agent to be used in the reduction reaction is used in an amount of 0.5 to 50 moles, preferably 0.6 to 10 moles, per mole of 6-nitroprostaglandin $E_1$ derivatives. The solvent may be used in an amount that is enough to cause the reaction proceed smoothly and the amount is usually 1 to 1,000 times, preferably 5 to 100 times the volume of the material compound (6-nitroprostaglandin $E_1$ derivatives). The reaction temperature varies depending upon the material, reagent, and solvent to be used in the reaction; however, the reaction is usually conducted in the range of $-78°$ C. to 150° C., preferably 0° C. to 100° C. The reaction time varies depending upon the conditions under which the reaction is carried out; however, desirably it should range somewhere between 0.1 and 48 hours, more desirably between 0.1 and 24 hours. The progress of reaction is traced by such a method as thin layer chromatography and the reaction can be regarded as completed when the material becomes imperceptible. After the reaction is over, the 6-nitroprostaglandin $F_1$ derivatives are separated and purified by subjecting the reaction mixture to the ordinary methods of treatment. For instance, the separation and purification are effected by a combined treatments of extraction, washing, drying, concentration, chromatography, etc.

The carbonyl group at the 9-position of the formula (I)-a is reduced and converted into a hydroxyl group in the abovementioned reduction reaction. In this case, obtained compounds are a mixture of the 6-nitroprostaglandin $F_1$ derivatives having a hydroxyl group of $\beta$-configuration and those having a hydroxyl group of $\alpha$-configuration, or by selection of reducing agents the 6-nitroprostaglandin $F_1$ derivatives having a hydroxyl group of only $\alpha$-configuration is obtained. When a mixture of 6-nitroprostaglandin $F_1\alpha$ derivatives and 6-nitroprostaglandin $F_1\beta$ derivatives is obtained, they can be usually separated from each other by means of thin layer chromatography, high performance liquid chromatography, etc. Thus obtained 6-nitroprostaglandin $F_1$ derivatives can be subjected to a reaction of removing the protective group and/or a hydrolysis reaction and/or a salt-forming reaction as mentioned hereinbefore, when occasion may require.

Investigations made by the inventors of the present invention have shown that these compounds of formula (I) provided by the invention which are represented by the formula (I)-1

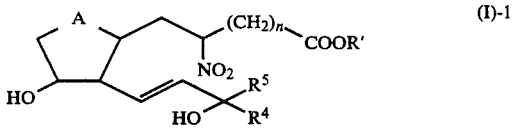

(I)-1 wherein $R^1$, $R^4$, n, A and $R^5$ are as defined above, have especially superior pharmacological activities, for example an activity of controlling vascular actions.

Thus, the present invention provides a pharmaceutical composition for controlling vascular actions, comprising (1) as an active ingredient a 6-nitroprostaglandin derivatives of the formula (I)-1, and (2) a pharmaceutically acceptable carrier.

Preferred compound as active ingredient is a 6-nitroprostaglandin E₁ derivatives of the following formula (I)-1-a

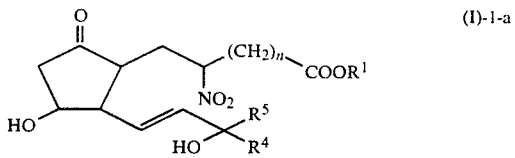

wherein $R^1$, $R^4$, n and $R^5$ are as defined above.

The active compound in accordance with this invention has an activity of controlling vascular actions such as blood pressure lowering action, platelet aggregation inhibiting action, ulcer-formation inhibiting action, etc. and has better selective activity than natural prostaglandin $E_1$.

The active compound of this invention can be administered to a warm-blooded animal such as humans or other animals whose vascular actions require control. The active compound of this invention can be administered for preventive or therapeutic purposes to warm-blooded animals whose vascular actions require control. The active compound of this invention can be administered to subjects for vasodilation, blood pressure lowering or antithrombosis and also for controlling various conditions such as angina pectories, arrerios-clerosis, myocardial infarction, endotoxin shock, pulmonary hypertension, cerebral apoplexy, transient ischemic attack, thrombycytopenic purpura, deep vein thrombosis and peripheral vascular diseases. The active compound of this invention can also be administered for inhibition ulcer-formation, asthma or metastasis of malignant tumors.

The 6-nitroprostaglandin derivatives of the present invention can be administered orally or parenterally such as percutaneously, subcutaneously, intramuscularly, intravenously, vaginally, reactally, etc.

As the form of preparations for oral administration, tablet, pill, granule, powder, solution, suspension, and capsule, for instance, may be mentioned.

Tablets can be formed according to the ordinary method by use of such excipients as lactose, starch, polyvinyl pyrrolidone, calcium carbonate, microcrystalline cellulose, silicic acid, etc., such binders as carboxymethyl cellulose, methyl cellulose, potassium phosphate, etc., such disintegrators as sodium alginate, sodium hydrogencarbonate, sodium lauryl sulfate, monoglyceride stearate, etc., such moisteners as glycerin, etc., such adsorbents as kaolin, colloidal cilicic acid, etc., and such lubricants as refined talc, powdered boric acid, etc. Pills, powder, granules can also be formed according to the ordinary method by use of the abovementioned excipients and other additive agents.

Solutions and suspensions can be prepared according to the ordinary method by use of such glyceryl esters as tricaprylin, triacetin, etc., such vegetable fats and oils as coconut oil, fractionated coconut oil, etc., purified water, such alcohols as ethanol, etc. Capsules can be prepared by filling capsules made from gelatin, etc. with granules, powder, and solution.

As the form of preparations for percutaneous administration, ointments and creams may be mentioned. Ointments can be prepared according to the ordinary method by use of such vegetable fats and oils as castor oil, olive oil, etc. and vaseline, etc. and creams can be prepared likewise by use of fats and oils and such emulsifying agents as diethylene glycol, sorbitan mono fatty acid ester, etc.

As the form of preparations for subcutaneous, intramuscular, and intravenous administration, there are injections prepared in the form of an aqueous or non-aqueous solution or of a suspension. Non-aqueous solutions and suspensions are usually prepared by use of, for instance, propylene glycol, polyethylene glycol, olive oil, ethyl oleate, etc., with antiseptics and/or stabilizers added thereto as case may require. Injections are sterilized by filtration through a bacterial filter or by mixing of a germicide effected appropriately.

As the form of preparations for vaginal administration, film preparations prepared by use of polyvinyl pyrrolidone, hydroxy propyl cellulose, etc. or ointments may be mentioned.

As the form of preparations for rectal administration such ordinary suppositories as gelatin soft capsules, etc. may be mentioned.

The 6-nitroprostaglandin derivatives which are the active compound of the present invention can also be allowed to be contained in the preparations as the inclusion compounds of α-, β-, or γ-cyclodextrins or their methylated cyclodextrins.

The active compound of this invention is administered, either singly or as the aforesaid pharmaceutical composition, or as a medicament in unit dosage form.

The dose of the active compound varies depending upon the type of the active compound, the subject to which it is administered, the conditions, age, sex, and body weight of the subject, or the route of administration. Usually it can be administered in a dose of about 0.01 μg to about 20 mg/kg of body weight/day. The dose may be administered once a day or in several portions, for example 2 to 6 times a day.

The 6-nitroprostaglandin derivatives provided by the present invention are useful as intermediate for the preparation of various prostaglandin compounds. That is, the 6-nitroprostaglandin derivatives can be converted into prostaglandin $E_1$ or $F_1$ derivatives or 6-oxo-prostaglandin $E_1$ or $F_1$ derivatives.

(A) Preparation of prostaglandin $E_1$ or $F_1$ derivatives from 6-nitroprostaglandin derivatives By making the 6-nitroprostaglandin derivatives of the following formula (I)

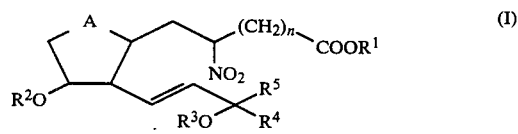

wherein A, n, $R^1$, $R^2$, $R^3$, $R^4$ and $R^5$ are as defined above,
react with tributyltin hydride or triphenyltin hydride in the presence of a radical initiating agent, and, if necessary, further subjecting the reaction product to a reaction of removing the protective group and/or a hydrolysis reaction and/or a salt-forming reaction, prostaglandin derivatives of the following formula (V)

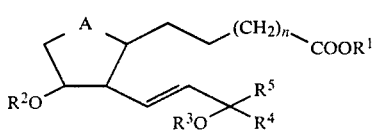

wherein A, n, $R^1$, $R^2$, $R^3$, $R^4$ and $R^5$ are as defined above,
can be prepared.

The amount of tributyltin hydride, or triphenyltin hydride to be used in the present invention is 0.5 to 50 moles, preferably 0.8 to 10 moles, more preferably 1.0 to 5 moles per mole of 6-nitroprostaglandin derivatives of said formula (I).

In the present invention, a proper radical initiating agent is used as a reaction assisting agent to allow the reaction to start. A radical initiating agent, which is used as a reaction assisting agent in a radical reduction reaction where tributyltin hydride or triphenyltin hydride are used, is conveniently used in general. As such radical initiating agents and means, $\alpha,\alpha'$-azobisisobutyronitrile, bis-t-butyl peroxide, potassium graphite, soidum amalgam, or irradiation with light, for instance, may be mentioned. As for the amount of a radical initiating agent, it is effective when it is used in the range of 0.05 to 20% by weight, preferably 0.1 to 5% by weight of tributyltin hydride or triphenyltin hydride.

The reaction is usually carried out in an atmosphere of an inert gas such as nitrogen and argon. The process of the present invention may be practiced by using tributyltin hydride as a solvent or any solvent that is used in an ordinary reduction reaction of tributyltin hydride may be used as a solvent in the process. As such solvents, such aromatic hydrocarbons as benzene, toluene, and xylene, such aliphatic hydrocarbons as hexane and heptane, and such ethers as diehtyl ether and tetrahydrofuran are used conveniently. The amount of a solvent is sufficient when used 0.5 to 50 times the volume of tributyltin hydride.

Though the reaction temperature varies depending upon the reaction assisting agent and reaction conditions, the reaction is usually conducted in the range of 0° to 150° C., preferably 80° to 120° C. The time required for carrying out the reaction also varies depending upon the reaction conditions including the amount of tributyltin hydride or triphenyltin hydride and reaction temperature and the termination of the reaction is determined while tracing the reaction by thin layer chromatography; however, when the reaction is conducted at 100° C., it is completed in 0.5 to 12 hours.

After the reaction is over, prostaglandin $E_1$ or $F_1$ derivatives expressed by said formula (V) can be isolated by subjecting the reaction mixture to extraction, washing, drying, chromatography, etc. according to ordinary techniques. The isolation can also be effected by directly subjecting the reaction mixture to chromatography after the removal of the solvent by distillation under reduced pressure.

The prostaglandin derivatives thus obtained may further be subjected to a reaction of removing the protective group and/or a hydrolysis reaction and/or a salt-forming reaction in the same way as mentioned before, as case may require. Of these derivatives, prostaglandin $E_1$ derivatives are especially useful compounds as pharmaceutical products.

(B) Preparation of 6-oxoprostaglandin $E_1$ or $F_1$ derivatives from 6-nitroprostaglandin derivatives (i) By allowing the 6-nitroprostaglandin derivatives of the following formula (I)

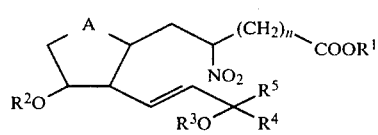

wherein A, n, $R^1$, $R^2$, $R^3$, $R^4$, and $R^5$ are as defined above,
to react with a trivalent titanium compound in the presence of a weakly basic compound and buffer salt, followed by a reaction of removing the protective group and/or a hydrolysis reaction and/or a salt-forming reaction as case may require, 6-oxoprostaglandin derivatives of the following formula (VI)

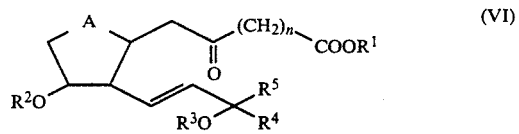

wherein A, n, $R^1$, $R^2$, $R^3$, $R^4$, and $R^5$ are as defined above,
are obtained.

Of the 6-oxoprostaglandin derivatives, 6-oxoprostaglandin $E_1$ derivatives (in case that A represents a carbonyl group in formula (VI)) have excellent pharmacological activities such as platelet aggregation inhibiting activity, blood pressure lowering activity, ulcerformation inhibiting activity, etc. and they are compound expected to be used for preparing pharmaceuticals (Japanese Patent Application Laid-Open No. 44639/79). Also, 6-oxoprostaglandin $F_1$ derivatives (in case that A represents a hydroxy methylene group in formula (VI)) are useful as diagnosticums (Advanced in Prostaglandin, Thromboxane, and Leuketriene Research, vol 11, 197 (1983), Raven Press N.Y.).

As the weakly basic compounds to be used in the present invention, basic compound which are less reactive to the cyclopentenone skeleton of 6-nitroprostaglandin derivatives and capable of abstracting hydrogen atom on carbon to which the nitro group is attached are desirable, and as examples of such weakly basic compounds, triphenylphosphine, tributylphosphine, tetrabutylammonium fluoride potassium fluoride, potassium carbonate, tetramethylguanidine, diisopropylamine, morpholine, pyrrolidine, piperidine, and triethylamine may be mentioned. Of these compound, triphenylphoshine is especially desirable.

By introduction of a weakly basic compound, 6-nitroprostaglandin derivatives are believed to be first converted into an active type.

As a trivalent titanium compound, an aqueous solution of commercially available titanium trichloride can be conveniently used. However, when the reaction is conducted by use of an aqueous solution of titanium trichloride alone, the pH value of the reaction system falls below 1, thus strongly acidifying the reaction mixture undesirably. It is, therefore, an ordinary practice to conduct said reaction while adjusting the pH in the neutral range (with pH 4 to 7, desirably near 6) by addition of a buffer salt.

As such a buffer salt, sodium formate, ammonium acetate, sodium acetate, potassium acetate, sodium succinate, sodium citrate, sodium tartrate, sodium phthalate, sodium monohydrogenphosphate, sodium dihydrogen phosphate, potassium monohydrogenphosphate, and potassium dihydrogenphosphate may be mentioned. Of them all, ammonium acetate is especially preferable.

The above-mentioned weakly basic compounds are usually used in an amount of 0.5 to 20 moles, preferably 1 to 10 moles, per mole of the 6-nitroprostaglandin derivative used in the reaction. Titanium trichloride is used in an amount of 1 to 20 moles, preferably 2 to 15 moles, more preferably 3 to 10 moles, per mole of the 6-nitroprostaglandin derivative. The amount of the buffer salt to be used varies depending upon its kind and the amount of titanium trichloride and the amount is determined while observing the change of pH value. In case where ammonium acetate is used, for instance, the pH value of the reaction solution can be adjusted near 6 when ammonium acetate is used in an amount of 6 moles per mole of titanium trichloride.

Another addition of an organic medium having a comparatively good water solubility to the reaction system produces a beneficial effect upon the smooth progress of the reaction. As such organic media, solvents of ether type such as diethyl ether, tetrahydrofuran, dimethoxyethane, and dioxane, or solvents of alcohol type such as methanol, ethanol, and isopropyl alcohol may be mentioned.

The reaction is usually conducted at a temperature in the range of 0° C. to 40° C., preferably 20° to 30° C. The reaction time varies depending upon the reaction conditions including the reaction temperature, amount of the reactants, and pH value. The termination of reaction is determined by tracing the reaction by means of analysis such as thin layer chromatography, etc. The reaction is usually completed in 1 to 48 hours when conducted at room temperature.

After the reaction is over, the obtained product is separated from the reaction solution and refined according to the ordinary methods, including for instance, extraction, washing, and chromatography or their combination.

In the way as mentioned above, the 6-nitroprostaglandin derivatives are transformed into 6-oxoprostaglandin derivatives and thus obtained 6-oxoprostaglandin derivatives may further be subjected to the aforementioned reaction of removing the protective group and/or hydrolysis reaction and/or salt-forming reaction as occasion may require.

(ii) 6-Oxoprostaglandin $E_1$ derivatives (in case that A represents a carbonyl group in formula (VI)) can also be prepared according to the following method.

A 4-substituted-2-cyclopentenone of the following formula (II)

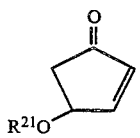

(II)

wherein $R^{21}$ is defined above, and an organocupper reagent resulting from a organolithum compound of the formula (III-1)

(III-1)

wherein $R^{31}$, $R^{41}$ and $R^5$ are as defined above, and a cuprous salt of the formula (III-2)

$$C u Q \qquad \text{(III-2)}$$

wherein Q is as defined above, are subjected to conjugation addition reaction in an aprotic organic solvent. The reaction product is then made to react with the nitroolefin compound of the formula (IV)

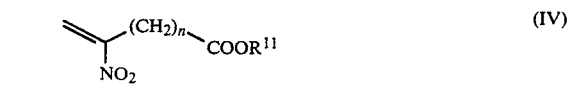

(IV)

wherein n and $R^{11}$ are as defined above, and then, without isolating the 6-nitroprostaglandin $E_1$ derivative, the reaction mixture is further made to (a) react with an acid compound, (b) react with a trivalent titanium compound, or (c) react with an oxidizing agent, and is furthermore subjected to reaction of removing the protective group and/or hydrolysis reaction and/or salt-forming reaction as occasion may require, thus obtaining 6-oxoprostaglandin $E_1$ derivatives of the following formula (V-a)

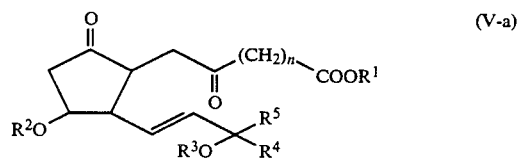

(V-a)

wherein n, $R^1$, $R^2$, $R^3$, $R^4$, and $R^5$ are as defined above.

Here in the above series of reactions, the process including the conjugation addition reaction conducted between the 4-substituted-2-cyclopentenone of formula (II) and the organocupper reagent in the aprotic inert organic solvent and the succeeding reaction with the nitroolefin compound can be conducted in the same way as mentioned before. After such series of reactions are over, the 6-nitroprostaglandin $E_1$ derivatives exist in the reaction system in the form of an active type. Therefore, in this method, it is not required to add a weakly basic compound to the reaction system as done in the method of (i) to convert the 6-nitroprostaglandin $E_1$ derivatives to active type, and then, without isolating the 6-nitroprostaglandin $E_1$ derivatives, by making the reaction with the nitroolefin compound of formula (IV) followed by (a) a reaction with an acid compound, (b) reaction with a trivalent titanium compound, or (c) reaction with an oxidizing agent conducted in the same reaction system, 6-oxoprostaglandin $E_1$ derivatives are obtained.

(a) Reaction with an Acid Compound

In the method in which an acid compound is used, an equimolecular quantity or more of hydrochloric acid per 4-substituted-2-cyclopentenone (preferably 0.5 to 6 normal, more preferably 1 to 4 normal hydrochloric acid) or sulfuric acid (preferably 1 to 12 normal, more preferably 3 to 6 normal sulfuric acid) is added to the reaction mixture, which contains an active-type 6-nitroprostaglandin $E_1$ derivatives formed in the reaction where 4-substituted-2-cyclopentenone is allowed to react with an organocupper reagent compound, followed by the reaction with nitroolefin, to effect a reaction. It is advisable to add an organic medium having a comparatively good water solubility to the reaction system in order to make the reaction proceed smoothly. As such organic media, solvents of ether type such as diethyl ether, tetrahydrofuran, dimethoxyethane and dioxane, or solvents of alcohol type and as methanol, ethanol, and isopropyl alcohol may be mentioned.

The reaction temperature varies to some degree depending upon the kind and concentration of the acid compound and the water-soluble organic solvent; however, the reaction is usually conducted in the range of temperature between $-20°$ C. and $80°$ C., preferably between $0°$ C. and $60°$ C., more preferably between $20°$ C. and $50°$ C. The reaction time also varies depending upon the reaction temperature and reaction conditions and the termination of reaction is determined by tracing the reaction by means of analytical method such as thin layer chromatography. The reaction is completed in about 0.5 hour to 5 hours when conducted at a temperature of $40°$ C.

(b) Reaction with a Trivalent Titanium Compound

In the method in which a trivalent titanium compound is used, the reaction can be conducted practically in the same method as described in the aforementioned (i) with the exception of not adding a weakly basic compound. As a trivalent titanium compound, an aqueous solution of an ordinary commercially available titanium trichloride can be directly used. It is desirable to conduct the reaction in the presence of a buffer salt. As the buffer salt, the same buffer salt as mentioned before can be used. In effecting the reaction, the pH value of the aqueous solution of titanium trichloride should be adjusted in the neutral range (pH 4~7, preferably around 6) by adding a buffer salt thereto and then the aqueous solution is added to the reaction system which contains the active type of 6-nitroprostaglandin $E_1$ derivatives.

The reaction is conducted using said titanium trichloride in an amount of 1 to 20 moles, preferably 2 to 15 moles, more preferably 3 to 10 moles, per mole of active type of 6-nitroprostaglandin $E_1$ derivatives. It is recommendable to further add a comparatively water-soluble organic medium to the reaction system to enhance the smooth proceeding of the reaction and as such organic media, solvents of ether type such as diethyl ether, tetrahydrofuran, dimethoxyethane and dixane, or solvents of alcohol type such as methanol, ethanol and isopropyl alcohol may be mentioned.

The reaction temperature is usually in the range of $0°$ C. for $40°$ C., preferably $20°$ C. to $30°$ C. The reaction time varies depending upon the reaction conditions such as the reaction temperature, amount of the reactants, pH value, etc. and the reaction is traced by such analytical means as thin layer chromatography, etc. to have its termination determined; however, the reaction is completed in 1 to 5 hours when carried out at room temperature.

(c) Reaction with an Oxidizing Agent

In the method in which an oxidizing agent is used, the reaction conditions to be adopted vary with the type of an oxidizing agent intended to be used. For instance, in a reaction where aqueous hydrogen peroxide is used as an oxidizing agent, aqueous hydrogen peroxide (desirably 10 to 30% aqueous hydrogen peroxide), which contains hydrogen peroxide in amounts equimolar with 4-substituted-2-cyclopentenone or more, preferably 5 to 20 moles per mole of it, is added to the reaction mixture containing the active type 6-nitroproslaglandin $E_1$ dirivatives which is formed in the reaction between 4-substituted-2-cyclopentenone and organocupper reagent and the suceeding reaction between thus obtained reaction product and nitroolefin, to effect the reaction. An organic medium having a comparatively good water solubility may be conveniently added to the reaction system so that the reaction may proceed smoothly. As such organic media, solvents of ether type such as diethyl ether, tetrahydrofuran, dimethoxyethane and dioxane, or solvents of alcohol type such as methanol, ethanol and isopropyl alcohol may be mentioned.

The reaction temperature varies more or less depending upon the type and concentration of the water-soluble organic medium used in the reaction; however, it is usually in the range of $-20°$ C. to $80°$ C., preferably $0°$ C. to $60°$ C., especially preferably $20°$ C. to $50°$ C. The reaction time also varies with the reaction temperature and reaction conditions and the termination of the reaction can be determined by tracing the reaction by analytical means including thin layer chromatography. The reaction is completed in about 0.5 to 8 hours when conducted at $40°$ C.

In case where tert-butyl hydroperoxide is used as an oxidizing agent, it is added in amounts equimolar with 4-substituted-2-cyclopentenone or more, preferably 5 to 20 moles per mole of it, to the reaction mixture containing active type 6-nitroprostaglandin $E_1$ derivatives to allow the reaction to start. The presence of a catalyst is necessary to carry on the reaction thoroughly and as such catalysts, vanadium (IV) oxyacetylacetonato, molybdenum pentacarbonyl, etc. may be mentioned. They are used in an amount of 0.1 to 20 mol %, preferably 1 to 10 mol % of tert-butyl hydroperoxide.

The reaction temperature varies depending upon the amount of tert-butyl hydroperoxide, types and amount of the catalyst to be used; however, the reaction is usually carried out in the range of $-20°$ to $100°$ C., preferably $0°$ C. to $80°$ C. The reaction time also varies depending upon the reaction temperature and reaction conditions and the termination of reaction is determined while tracing the reaction by analytical means of thin layer chromatography, etc.; however, the reaction is terminated in about 0.5 to 24 hours when conducted at a temperature of $40°$ C.

Besides the oxidizing agents exemplified in the above, pyridine-hexamethyl phosphor triamide complexes of molybdenum pentoxide, potassium permanganate, and cerium (IV) ammonium nitrate may also be mentioned as useful oxidizing agents.

After the reaction is over, the obtained product is separated from the reaction mixture and refined according to ordinary methods, such as extraction, washing, chromatography or combination thereof.

The desired 6-oxoprostaglandin $E_1$ derivatives are obtained in the way mentioned above. These 6-oxoprostaglandin $E_1$ derivatives may be subjected to the aforementioned reaction of removing the protective group and/or hydrolysis reaction and/or salt-forming reaction, if necessary.

The 6-oxoprostaglandin $E_1$ or $F_1$ derivatives obtained according to the preceding methods (i) and (ii) are exemplified below:

| | |
|---|---|
| (500) | 6-oxoprostaglandin $E_1$ |
| (502) | 15-methyl-6-oxoprostaglandin $E_1$ |
| (504) | 16-methyl-6-oxoprostaglandin $E_1$ |
| (506) | 17-methyl-6-oxoprostaglandin $E_1$ |
| (508) | 18-methyl-6-oxoprostaglandin $E_1$ |
| (510) | 19-methyl-6-oxoprostaglandin $E_1$ |
| (512) | 20-methyl-6-oxoprostaglandin $E_1$ |
| (514) | 20-ethyl-6-oxoprostaglandin $E_1$ |
| (516) | 20-propyl-6-oxoprostaglandin $E_1$ |
| (518) | 16-ethyl-6-oxoprostaglandin $E_1$ |
| (560) | 17-ethyl-6-oxoprostaglandin $E_1$ |
| (562) | 15,16-dimethyl-6-oxoprostaglandin $E_1$ |
| (564) | 16,17-dimethyl-6-oxoprostaglandin $E_1$ |
| (566) | 16,20-dimethyl-6-oxoprostaglandin $E_1$ |
| (568) | 17,20-dimethyl-6-oxoprostaglandin $E_1$ |
| (560) | 16,16,20-triethyl-6-oxoprostaglandin $E_1$ |
| (562) | 17-methyl-20-ethyl-6-oxoprostaglandin $E_1$ |
| (564) | 15-cyclopentyl-w-pentanor-6-oxoprostaglandin $E_1$ |
| (566) | 15-cyclohexyl-w-pentanor-6-oxoprostaglandin $E_1$ |
| (568) | 15-(2,3-diethyl)cyclopropyl-w-pentanor-6-oxoprostaglandin $E_1$ |
| (570) | 15-(2,2-dimethyl)cyclopentyl-w-pentanor-6-oxoprostaglandin $E_1$ |
| (572) | 15-(4-t-butyl)cyclohexyl-w-pentanor-6-oxoprostaglandin $E_1$ |
| (574) | 16-cyclopentyl-w-tetranor-6-oxoprostaglandin $E_1$ |
| (576) | 17-cyclopentyl-w-trinor-6-oxoprostaglandin $E_1$ |
| (578) | 18-cyclopentyl-w-dinor-6-oxoprostaglandin $E_1$ |
| (560) | 16-cyclohexyl-w-tetranor-6-oxoprostaglandin $E_1$ |
| (562) | 17-cyclohexyl-w-trinor-6-oxoprostagandine $E_1$ |
| (564) | 18-cyclohexyl-w-dinor-6-oxoprostaglandin $E_1$ |
| (566) | 18-oxa-6-oxoprostaglandin $E_1$ |
| (568) | 16-phenyl-w-tetranor-6-oxoprostaglandin $E_1$ |
| (560) | 17-phenyl-w-trinor-6-oxoprostaglandin $E_1$ |
| (562) | 16-phenoxy-w-tetranor-6-oxoprostaglandin $E_1$ |
| (564) | methyl ester of (500) |
| (566) | methyl ester of (502) |
| (568) | methyl ester of (504) |
| (570) | methyl ester of (506) |
| (572) | methyl ester of (508) |
| (574) | methyl ester of (510) |
| (576) | ethyl ester of (512) |
| (578) | ethyl ester of (514) |
| (580) | ethyl ester of (516) |
| (582) | ethyl ester of (518) |
| (584) | sodium salt of (520) |
| (586) | sodium salt of (522) |
| (588) | sodium salt of (524) |
| (590) | sodium salt of (526) |
| (592) | 11,15-bis(t-butyldimethylsilyl)ether of (528) |
| (594) | 11,15-bis(t-butyldimethylsilyl)ether of (530) |
| (596) | 11,15-bis(t-butyldimethylsilyl)ether of (532) |
| (598) | 11,15-bis(t-butyldimethylsilyl)ether of (534) |
| (600) | 11,15-bis(t-butyldimethylsilyl)ether of (536) |
| (602) | 6-oxoprostaglandin $F_{1\alpha}$ |
| (604) | 15-methyl-6-oxoprostaglandin $F_{1\alpha}$ |
| (606) | 16-methyl-6-oxoprostaglandin $F_{1\alpha}$ |
| (608) | 17-methyl-6-oxoprostaglandin $F_{1\alpha}$ |
| (610) | 20-methyl-6-oxoprostaglandin $F_{1\alpha}$ |
| (612) | 17,20-dimethyl-6-oxoprostaglandin $F_{1\alpha}$ |
| (614) | 15-cyclopentyl-w-pentanor-6-oxoprostaglandin $F_{1\alpha}$ |
| (616) | 15-cyclohexyl-w-pentanor-6-oxoprostaglandin $F_{1\alpha}$ |
| (618) | 16-cyclopentyl-w-tetranor-6-oxoprostaglandin $F_{1\alpha}$ |
| (620) | 18-cyclohexyl-w-dinor-6-oxoprostaglandin $F_{1\alpha}$ |
| (622) | 18-oxa-6-oxoprostaglandin $F_{1\alpha}$ |
| (624) | 16-phenoxy-w-tetranor-6-oxoprostaglandin $F_{1\alpha}$ |
| (626) | methyl ester of (602) |
| (628) | ethyl ester of (604) |
| (630) | propyl ester of (606) |
| (632) | sodium salt of (608) |
| (634) | sodium salt of (610) |
| (636) | 11,15-bis(t-butyldimethylsilyl)ether of (612) |
| (638) | 11,15-bis(t-butyldimethylsilyl)ether of (614) |

As described in detail in the above, the 6-nitroprostaglandin derivatives provided by the present invention also act as intermediates for the making of prostaglandin $E_1$ or $F_1$ derivatives and 6-oxoprostaglandin $E_1$ or $F_1$ derivatives and are very useful compounds.

The following Examples illustrate the present invention more specifically.

EXAMPLE 1 dl-11,15-bis(t-butyldimethylsilyl)6-nitroprostaglandin $E_1$ Methyl Ester and its 15-epimer A pentane solution (1.2 ml, 2.6 mmol) of 2.2M t-butyllithium was added to an ether solution (10 ml) of (E)-dl-3-t-butyldimethylsilyloxy-1-iodo-1-octene (478 mg, 1.3 mmol) at −78° C. and the mixed solution was stirred for 2 hours. An ether solution (3 ml) of cuprous iodide (248 mg, 1.3 mmol) and tributylphosphine (578 mg 2.9 mmol) was added to this mixed solution and the solution was stirred at −78° C. for 1 hour. An ether solution (6 ml) of dl-4-t-butyl-dimethylsilyloxy-2-cyclopentenone (212 mg, 1.0 mmol) was added to the solution and was stirred at −78° C. for 15 minutes and then at −40° C. for 1 hour. After the solution was cooled to −78° C., an ether solution (5 ml) of methyl 6-nitro-6-heptenoate (187 mg, 1.0 mmol) was added thereto. The resulting mixture was stirred for 15 minutes at −78° C., and was further stirred at −40° C. for 1 hour and at −20° C. for 30 minutes. After the addition of ether, the reaction mixture was washed first with an aqueous solution of ammoniac ammonium chloride and then with an aqueous solution of ammonium chloride, followed by drying over magnesium sulfate and concentrating, to obtain 1.74 g of a crude product. This product was subjected to column chromatography (hexane:ethyl acetate =10:1) on silica gel to obtain a mixture (232 mg, 0.362 mmol, 36%) of dl-11,15-bis(t-butyldimethylsilyl)-6-nitroprostaglandin $E_1$ methyl ester and its 15-epimer.

NMR(CDCl$_3$, δ(ppm)); 0.06 (12H, s), 0.84~0.86 (21H), 1.1~2.6 (22H, m), 3.61 (3H, s), 3.8~4.3 (2H, m), 4.5~5.2 (1H, m), 5.35~5.55 (2H, m).

IR (liquid film, cm$^{-1}$); 1740, 1555, 1460, 1440, 1360, 1255, 1160, 1100, 1005, 970, 875, 860, 840, 810, 775.

Mass (20 eV; m/e, %); 626 (1, M-Me), 610 (4, M-OMe), 584 (29, M-$^t$Bu), 570 (38), 553 (23), 498 (17), 493 (20), 464 (22), 438 (26), 421 (28), 405 (20), 330 (40), 299 (36), 277 (100), 245 (20), 215 (20), 175 (25), 75 (94).

EXAMPLE 2

11,15-bis(t-butyldimethylsilyl)-6nitroprostaglandin $E_1$ Methyl Ester 11,15-bit(t-butyldimethylsilyl)-6-nitroprostaglandin $E_1$ methyl ester (656 mg, 1.023 mmol, 34%) was obtained from (E)-3(S)-t-butyldimethyl-silyloxy-1-iodo-1-octene (1.21 g, 3.3 mmol; [α]$_D^{21}$ 30.6° ) and 4(R)-t-butyl-dimethylsilyloxy-2-cyclopentenone (636 mg, 3.0 mmol) according to the same method as Example 1. NMR, IR, and Mass of this compound coincided with those of the compound obtained in Example 1.

[α]$_D^{21}$ −22.3° (MeOH, c 0.71)

Example 3

6-nitroprostaglandin $E_1$ Methyl Ester

The 11,15-bis(t-butyldimethylsilyl)-6-nitroprostaglandin $E_1$ methyl ester (494 mg, 0.77 mmol) obtained in Example 2 was dissolved in acetonitrile (10 ml). 1 ml of 47% hydrofluoric acid was added to the solution and was stirred at room temperature for 1.5 hours. The reaction mixture was neutralized by use of an aqueous solution of sodium hydrogencarbonate, extracted with ethyl acetate, washed with saline solution, and dried over magnesium sulfate to obtain 290 mg of a crude product. This product was separated by column chromatography (hexane:ethyl acetate=4) on silica gel to obtain 6-nitroprostaglandin $E_1$ methyl ester (256 mg, 0.62 mmol, 81%).

NMR (CDCl$_3$, 67 (ppm)); 0.87 (3H, m), 1.0~3.1 (24H, m), 3.57 (3H, s), 3.8~4.2 (2H, m), 4.5~5.1 (1H, m), 5.3~5.6 (2H, m).

IR (liquid film, cm$^1$); 1740, 1550, 1435, 1360, 1245, 1200, 1160, 1075, 1015, 975.

Mass (20 eV; m/e, %); 395 (3, M-H$_2$O), 377 (3), 364 (3), 347 (8), 342 (9), 324 (27), 315 (15), 299 (13), 298 (12), 277 (38), 245 (40), 227 (22), 217 (42), 199 (27), 99 (100), 71 (38).

$[\alpha]_D^{21}$ −24.5° (MeOH, c 0.20)

EXAMPLE 4 to 7

The following compounds were prepared according to Examples 2 and 3. Their spectra are compiled in Table 1. These compounds are 16,17,18,19,20-pentanor-15-cyclohexyl-6-nitroprostaglandin $E_1$ methyl ester (Example 4, 48% yield), 16,17,18,19, 20 -pentanor-15-cyclopentyl-6-nitroprostagandin $E_1$ methyl ester (Example 5, 46% yield), 17(R),20-dimethyl-6-nitroprostaglandin $E_1$ methyl ester (Example 6, 52% yield), and 17(S),20-dimethyl-6-nitroprostaglandin $E_1$ methyl ester (Example 7, 58% yield).

TABLE 1

| Example | NMR (CDCl$_3$, δ (ppm)) | IR (liquid film, cm$^{-1}$) | Mass (20 eV,m/e) |
|---|---|---|---|
| 4 | 0.9~3.1 (27H, m), 3.58 (3H, s), 3.8~4.2 (2H, m), 4.5~5.1 (1H, m), 5.3~5.6 (2H, m). | 1740, 1550, 1245, 1200, 1160, | 307 (M—M$_2$O), 389 (M—2H$_2$O) |
| 5 | 0.9~3.1 (25H, m), 0.60 (3H, s), 3.8~4.2 (2H, m), 4.5~5.1 (1H, m), 5.3~5.6 (2H, m). | 1740, 1550, 1245, 1200, 1160, 1075. | 393 (M—H$_2$O), 375 (M—2H$_2$O). |
| 6 | 0.9 (6H, m), 1.0~3.0 (25H, m), 3.65 (3H, s), 3.9~4.3 (2H, m), 4.5~5.1 (1H, m), 5.3~5.6 (2H, m). | 1740, 1550, 1245), 1200, 1160, 1075. | 423 (M—H$_2$O), 405 (M—2H$_2$O). |
| 7 | 0.9 (6H m), 1.0~3.0 (25H, m), 3.65 (3H, s), 3.9~4.3 (2H, m), 4.5~5.1 (1H, m), 5.3~5.6 (2H, m). | 1740, 1550, 1245, 1200, 1160, 1075. | 423 (M—H$_2$O), 405 (M—2H$_2$O). |

EXAMPLE 8

11,15-bis(t-butyldimethylsilyl)-17(S),20-dimethyl-6-nitroprostaglandin $E_1$ Methyl Ester 11,15-bis(t-butyldimethylsilyl)-17(S),20-dimethyl-6-nitroprostaglandin $E_1$ methyl ester (144 mg, 0.21 mmol, 21%) was obtained by the reaction of (E)-3(S)-t-butyldimethylsilyloxy-1-iodo-5(S)-methyl-1-nonene (476 mg, 1.2 mmol), 4(R)-t-butyldimethylsilyloxy-2-cyclopentenone (212 mg, 1.0 mmol), methyl 6-nitro-6-heptenoate (374 mg, 2.0 mmol) in the presence of copper complex resulting from 1-pentylcopper (I) (157 mg, 3.3 mmol) according to the same method as Examples 1 and 2. NMR, IR, and Mass of this compound coincided with those of the compound obtained in Example 7.

EXAMPLE 9

11,15-bis(t-butyldimethylsilyl)-6-nitroprostaglandin $F_1\alpha$ and $F_1\beta$ Methyl Ester A sodium borohydride (760 mg, 20 mmol) was added to a methanol (200 ml) cooled to 0° C. and the resulting mixture was stirred for 3 minutes. A methanol solution (50 ml) of 11,15-bis(t-butyldimethylsilyl)-6-nitroprostaglandin $E_1$ methyl ester (617 mg, 0.963 mmol) was added to the solution and the solution was stirred at 0° C. for 40 minutes. Then, a saturated aqueous solution of ammonium chloride was added, and methanol in the mixture was evaporated. The residue was extracted three times with ethylacetate (100 ml). The separated organic layer was washed with aqueous sodium chloride, dried over magnesium sulfate, and concentrated to give a mixture (588 mg, 0.914 mmol, 95%) of 11,15-bis(t-butyldimethylsilyl)-6-nitroprostaglandin $F_1\alpha$ methyl ester and $F_1\beta$ methyl ester.

NMR (CDCl$_3$, δ (ppm)); 0.06 (12H, s), 0.84 (21H), 1.1~2.4 (23H, m), 3.60 (3H, s), 3.8~4.2 (3H, m),~4.7 (1H, b), 5.25~5.45 (2H, m).

IR (liquid film, cm$^{-1}$); 3500, 2950, 2860, 1735, 1545, 1460, 1435, 1360, 1250, 1060, 1000, 965, 835, 770

Mass (20 eV; m/e, %); 586 (M-57, 33), 572 (34), 555 (35), 494 (47), 463 (47), 454 (52), 440 (56), 423 (42), 407 (40), 362 (32), 333 (34), 315 (100), 215 (60), 201 (43), 189 (44), 189 (91), 175 (54), 171 (41), 99 (53), 75 (53).

Example 10

11,15-bis(t-butyldimethylsilyl)-6-nitro-2,3-dinorprostaglandin $E_1$ Methyl Ester:

11,15-bis(t-butyldimethylsilyl)-6-nitro-2,3-dinorprostaglandin $E_1$ methyl ester (43%) was obtained from methyl 4-nitro-4-pentenoate according to the same method as Example 1.

NMR (CDCl$_3$, δ (ppm)); 0.06 (12H, s), 0.86 (21H, m), 1.1~2.6 (18H, m), 3.61 (3H, s), 3.8~4.3 (2H, m), 4.5~5.1 (1H, m), 5.35~5.55 (2H, m).

IR (liquid film, cm$^{-1}$); 1740, 1555, 1460, 1440, 1360, 1255, 1160, 1100, 1005, 970, 875, 860, 840, 810, 775.

Mass (20 eV); 598 (M-Me, 2), 582 (M-OMe, 2), 556 (M-$^t$Bu, 31).

EXAMPLE 11

In Vitro Inhibitory Activity of Platelet Aggregation

The in vitro platelet aggregation inhibiting activity of the compounds of the invention were examined by using rabbits. Blood was withdrawn from the ear vein of Japanese domestic white male rabbits weighing 2.5 to 3.5 kg. A mixture of a 3.8% trisodium citrate solution and the blood in a ratio of 1:9 was centrifuged at a speed of 1000 rpm for 10 minutes. The upper layer was separated as platelet-rich plasma (PRP). The lower layer was further centrifuged at a speed of 28000 rpm for 10 minutes. The upper layer was separated as platelet-poor plasma (PPP). The number of platelets was adjusted to $6\times10^5/\mu l$ to $7\times10^5/82$ l by diluting the PRP with PPP. 25 microliters of the test compounds prepared as shown below was added in an amount of 25 to 250 microliters of PRP after the adjustment, and the mixture was preincubated at 37° C. for 2 minutes, and then 10 μM (final) of ADP was added. By using an aggregometer, changes in transmission were recorded.

The drug was dissolved in ethanol to a concentration of 10 mg/ml, and successively diluted with phosphate buffer (pH 7.4) prior to use.

The rate of inhibition of platelet aggregation was determined from the following equation.

$$\text{Inhibition rate (\%)} = \left(1 - \frac{T}{T_0}\right) \times 100$$

$T_o$: the transmittance of the system containing the phosphate buffer,
T: The transmittance of the system to which the test drug was added.

The minimum concentration of the drug which inhibited more than 50% of platelet aggregation was shown as an $IC_{50}$ value. The result are shown in Table 2.

TABLE 2

| Inhibitory activity of platelet aggregation | |
|---|---|
| Test compound | $IC_{50}$ (μg/ml) |
| 17(S),20-dimethyl-6-nitroprostaglandin $E_1$ methyl ester | 0.017 |
| 6-nitroprostaglandin $E_1$ methyl ester | 4.5 |

EXAMPLE 12

Measurement of the Hypotensive Activity

The actions of the 6-nitroprostaglandin $E_1$ derivatives of the invention on the blood pressure and heart beat rate of rats were examined by intravenous injection under anesthesia.

Male wister rats weighing about 250 g were used. Urethane (500 mg/kg) and α-chloralose (100 mg/kg) were intraperitoneally administered to the rats. The rats were anesthetized and fixed in place.

Each of the test compounds was dissolved in a small amount of ethanol and diluted with physiological saline to adjust the final ethanol concentration to not more than 5%. The solution was intravenously injected into the rats through a catheter inserted into the femoral vein.

The blood pressure of the rats were measured by a pressure transducer through a catheter inserted into the carotid artery of the rats. The heart beat rate was determined from the blood pressure pulse.

The action of the test compound on the blood pressure was expressed as the dosage (p-ED$_{Z20}$, μg/kg) of the test compound which caused a 20% lowering of the mean blood pressure before administration of the compound. The action of the test compound on the heart rate was expressed as the dosage (H-ED$_{10}$, μg/kg) of the test compound which caused a 10% increase of the heart rate from the heart beat rate before administration of the test compound.

The results are shown in Table 3.

TABLE 3

| | Hypotensive activity | |
|---|---|---|
| Test compound | P-ED$_{20}$ (μg/kg i.v.) | H-ED$_{10}$ (μg/kg i.v.) |
| 6-nitroprostaglandin $E_1$ methyl ester | 10 | >10 |
| 17(S),20-dimethyl-6-nitroprostaglandin $E_1$ methyl ester | 0.4 | >10 |

EXAMPLE 13

Measurement of Inhibitory Activity on Indomethacin Ulcer

Seven week-oil wistar-strain male rats (body weight 200 to 220 g) were fasted for 24 hours but water was provided freely, and then used in the following experiment.

Each of the test compounds suspended in phosphate Buffers (pH 7.4) was orally administered to the rats, and 30 minutes later, indomethacin was orally administered in a dose of 20 mg/kg. Six hours later, the animals were sacrificed. The abdomen was cut open, and the stomach was removed. 1% Even's blue was injected in an amount of 0.5 ml/rat into the rats through the tail vein under ether anesthesia 10 minutes before sacrificing.

12 ml of a 1% formalin was injected into the stomach and the stomach was further dipped in 1% formaline for about 10 minutes for the fixation. The stomach was cut open on the side of the greater curvature, and spread on a glass plate. The lengths of ulcers generated in the glandular stomach were measured by using a solid microscope. The sum of the lengths of the ulcers for each nimal was used as the ulcer index. The ulcer inhibiting ratio of the test compound was calculated in accordance with the following equation.

$$\text{Ulcer inhibiting ratio (\%)} = \frac{\text{Ulcer index of a control group} - \text{Ulcer index of a group to which the test compound was administered}}{\text{Ulcer index of the control group}} \times 100$$

The control group was given phosphate buffer saline (pH 7.4) indomethacin alone.

The results are given in Table 4.

TABLE 4

| Inhibitory activity on indomethacin ulcer | | | | |
|---|---|---|---|---|
| Test compound | Dose (μg/kg) oral | Number of animals | Ulcer index (mm) | Inhibition (%) |
| Control | DBS | 8 | 14.3 ± 3.1 | — |
| 17(S),20-dimethyl-6-nitroprostaglandin $E_1$ methyl ester | 3 | 8 | 12.5 ± 3.2 | 12.6 |
| | 10 | 8 | 7.0 ± 1.8 | 51.0 |
| | 30 | 8 | 2.8 ± 1.2** | 80.4 |

**P < 0.01

EXAMPLE 14

Production of Tablets

Tablets were produced each of which had the following composition.

| Active component | 5 μg |
|---|---|
| Lactose | 300 mg |

| | |
|---|---|
| Potato starch | 80 mg |
| Polyvinyl pyrrolidone | 10 mg |
| Magnesium stearate | 5 mg |
| | 395 mg in total |

The active ingredient, lactose andd potate starch were mixed, and the mixture was equally watted with a 20% ethanol solution of polyvinyl pyrrolidone. The wet mixture was passed through a 20-mesh screen, and dried at 45° C. Then, the dried particles were again passed through a 20-mesh screen. The resulting granules were mixed with magnesium stearate, and compressed into tablets.

6-Nitroprostaglandin $E_1$ methyl ester was used typically as the active ingredient.

EXAMPLE 15

Production of Powder

A powder was prepared in accordance with the following formulation.

| | |
|---|---|
| Active ingredient | 10 μg |
| Lactose | 100 mg |
| Corn starch | 100 mg |
| Hydrocypropyl cellulose | 10 mg |
| | 210 mg |

The active ingredient, lactose and corn starch were mixed, and an aqueous solution of hydroxypropyl cellulose was added. The mixture was dried to form a dust powder.

6-Nitroprostaglandin $E_1$ methyl ester was used typically as the active ingredient.

EXAMPLE 16

Production of Capsules

Hard gelatin capsules were produced each of which had the following composition.

| | |
|---|---|
| Active ingredient | 10 μg |
| Microcrystalline cellulose | 300 mg |
| Amorphous silica | 5 mg |
| | 305 mg in total |

The active ingredient in finely powdered form, the microcrystalline cellulose and unpressed amorphous silica were dully mixed, and the mixture was filled into hard gelatin capsules.

7(S),20-Dimethyl-6-nitroprostaglandin $E_1$ methyl ester was used typically as the active ingredient.

EXAMPLE 17

Production of Soft Capsules 1 mg of 6-nitroprostaglandin $E_1$ methyl ester was dissolved in 60 g of fractionated coconut oil and soft capsules were produced by use of a soft gelatin capsule making machine, each capsule being made to contain 1 μg of 6-nitroprostaglandin $E_1$ methyl ester.

EXAMPLE 18

(A) Preparation of 6-oxoprostaglandin $E_1$ derivatives from 6-nitroprostaglandin $E_1$ derivatives (i) dl-11,15-bis(t-butyldimethylsilyl)-6-oxoprostaglandin $E_1$ Methyl Ester and its 15-epimer (a) Triphenylphosphine (173 mg, 0.66 mmol) was added to tetrahydrofuran solution (5 ml) of a mixture (144 mg, 0.22 mmol) consisting of dl-11,15-bis(t-butyldimethylsilyl)-6-nitroprostaglandin $E_1$ methyl ester and its 15-epimer and the admixture was stirred at room temperature for 15 minutes. An aqueous solution prepared by dissolving ammonium acetate and an aqueous solution of 25% titanium trichloride (1.64 ml, about 2.64 mmol) (1.22 g, 15.8 mmol) in water (2 ml), and methanol (5 ml was added thereto and the mixture was stirred at room temperature for 5 hours. An aqueous solution of saturated sodium hydrogencarbonate was added to the reaction solution and was extracted with ethyl acetate. Then the obtained organic layer was washed with a saturated saline solution, dried over magnesium sulfate, and concentrated to give 324 mg of a crude product. The crude product was subjected to preparative thin-layer chromatography (hexane:ethyl acetate =3:1) to obtain a mixture (42 mg, 0.068 mmol, 32%) of dl-11,15-bis(t-butyl dimethylsilyl)-6-oxoprostaglandin $E_1$ methyl ester and its 15-epimer.

NMR (CDCl$_3$, δ (ppm)); 0.03 (12H, s), 0.86 (21H), 1.1~1.7 (12H), 2.15~2.70 (10H), 3.60 (3H, s), 3.85~4.20 (2H, m), 5.35~5.60 (2H, m).

IR (liquid film, cm$^{-1}$); 2960, 2940, 2860, 1745, 1720, 1460, 1435, 1405, 1360, 1250, 1155, 1100, 1000, 965, 935, 865, 835, 805, 775, 640.

MS (20 eV; m/e , %); 553 (0.5), 478 (3), 422 (4), 421 (12), 407 (4), 403 (4), 389 (3), 371 (3), 321 (8), 297 (3), 289 (2), 269 (3), 215 (4), 203 (3), 143 (4), 132 (4), 111 (4), 76 (9), 75 (100).

(b) In the same way as preceding (a), tributylphosphine (74 mg, 0.37 mmol) was added to a tetrahydrofuran solution (5 ml) of a mixture (39 mg, 61 μmol) consisting of dl-11, 15-bis(t-butyldimethylsilyl)-6-nitroprostaglandin $E_1$ methyl ester and its 15-epimer and was stirred at room temperature for 15 minutes. Thereafter, an aqueous solution prepared by dissolving ammonium acetate (305 mg, 3.96 mmol) and an aqueous solution of 25% titanium trichloride (0.41 ml, about 0.66 mmol) in 2 ml of water was added thereto and the mixture was stirred at room temperature for another 5 hours. The reaction mixture was subjected to the same work-up as (a) to give 122 mg of a crude product. The crude product was subjected to preparative thin-layer chromatography (hexane:ethyl acetate =3:1) to obtain the corresponding 6-oxo compound (8 mg, 13 umol, 21%). The respective spectra of this compound perfectly coincided with those obtained in (a). (c) In the same way as preceding (a), tetramethylguanidine (107 mg, 0.93 mmol) was added to a dimethoxyethane solution (5 ml) of a mixture (40 mg, 62 μmol) consisting of dl-11,15-bis(t-butyldimethylsilyl)-6-nitroprostaglandin $E_1$ methyl ester and its 15-epimer and was stirred at room temperature for five minutes. An aqueous solution prepared by dissolving ammonimum acetate (305 mg, 3.96 mmol) and an aqueous solution of 25% titanium trichloride (0.41 ml, about 0.66 mmol) in 2 ml of water was added thereto and the mixture was stirred at room temperature for another 5 hours. The reaction mixture was subjected to the same work-up as (a) to give 60 mg of a crude product. This product was subjected to preparative thin-layer chromatography (hexane:ethyl acetate =3:1) to obtain the corresponding 6-oxo compound (6 mg, 9.8 μmol, 16%). The respective spectra of this compound perfectly coincided with those obtained in (a).

(d) Similar to the case of (a), an aqueous solution prepared by dissolving ammonium acetate (610 mg, 7.92 mmol) and an aqueous solution of 25% titanium trichloride (0.82 ml, about 1.32 mmol) in 2 ml of water was added to a methanol solution (3 ml) of a mixture (72 mg, 0.11 mmol) consisting of dl-11,15-bis(t-butyldimethylsilyl)-6-nitroprostaglandin $E_1$ methyl ester and its 15-epimer and the mixture was stirred at room temperature for 20 hours. The same work-up as (a) was carried out to give a crude product, which was then separated by chromatographic technique to give the corresponding 6-oxo compound (13 mg, 0.021 mmol, 19%). The respective spectra of this compound perfectly coincided with those obtained in (a).

(ii) 6-Oxoprostaglandin $E_1$ Methyl Ester

In the same way as (i), (a), 11,15-bis(t-butyldimethylsilyl)-6-nitroprostaglandin $E_1$ methyl ester (192 mg, 0.30 mmol; $[\alpha]_D^{21}$ −22.3° (c 0.71, CH$_3$OH)) was dissolved in isopropyl alcohol (10 ml). triphenylphosphine (393 mg, 1.5 mmol) was added to the solution and stirred at room temperature for 15 minutes. An aqueous solution prepared by dissolving ammonium acetate (6.1 g, 7.9 mmol) and an aqueous solution of 25 % titanium trichloride (0.82 ml, 1.32 mmol) in 1 ml of water was added thereto and the mixture was stirred at room temperature for 5 hours. Thereafter, the reaction mixture was subjected to the same work-up as (i), (a) and the resulting crude product was subjected to preparative thin-layer chromatography (hexane:ethyl acetate =3:1) to obtain 11,15-bis(t-butyldimethylsilyl)-6-oxoprostaglandin $E_1$ methyl ester (61 mg, 0.10 mmol, 34%). NMR, IR, MS, and TLC of this compound perfectly coincided with those of the dl compound obtained in (i), (a).

The abovementioned 11,15-bis(t-butyldimethylsilyl)-6-oxoprostaglandin $E_1$ methyl ester (61 mg, 0.10 mmol) was dissolved in 10 ml of acetonitrile, to which 0.25 ml of pyridine and then 0.5 ml of hydrogen fluoride-pyridine were added. The mixture was then stirred at room temperature for 3 hours. After the reaction solution was neutralized with an aqueous solution of saturated sodium hydrogencarbonate, it was extracted with ethyl acetate and the separated organic layer was washed with a saturated saline solution dried over magnesium sulfate, and concentrated under reduced pressure to give 55 mg of a crude product. This crude product was subjected to preparative thin-layer chromatography (hexane:ethyl acetate =1:4) to obtain 6-oxoprostaglandin $E_1$ methyl ester (28 mg, 0.074 mmol, 74%).

NMR (CDCl$_3$, δ (ppm)); 0.87 (3H), 1.1~1.7 (12H, m), 2.0~3.0 (12H, m), 3.63 (2H, s), 3.7~4.3 (2H, m), 5.45~5.65 (2H, m).

IR (liquid film, cm$^{-1}$); 3400, 2950, 2870, 1740, 1720, 1435, 1410, 1370, 1250, 1200, 1160, 1075, 1020, 970, 730.

$[\alpha]_D^{22}$ −41° (c 0.62, CH$_3$OH). mp 41~42° C. (recrystallization from hexane-ether)

(iii) 11,15-bis(t-butyldimethylsilyl)-17(S),20-dimethyl-6-oxoprostaglandin $E_1$ methyl ester In accordance with the method of (i), (a), 11,15-bis(t-butyldimethylsilyl)-17(S),20-dimethyl-6-nitroprostaglandin $E_1$ methyl ester (308 mg, 0.46 mmol; $[\alpha]_D^{20}$ −15.7° (c 0.68, CH$_3$OH)) was dissolved in tetrahydrofuran (10 ml) and triphenylphosphine (482 mg, 1.84 mmol) was added thereto. The mixture was stirred at room temperature for 30 minutes. An aqueous solution prepared by dissolving ammonium acetate (1.22 g, 15.8 mmol) and an aqueous solution of 25% titanium trichloride (1.64 ml, 2.64 mmol) in 2 ml of water added to the reaction solution and the mixture was stirred at room temperature for 12 hours. Then the reaction solution went through the same work-up as (i), (a), and the obtained crude product was subjected to preparative thin-layer chromatography (hexane:ethyl acetate =4:1) to give 11,15-bis(t-butyldimethylsilyl)-17(S),20-dimethyl-6-oxoprostaglandin $E_1$ methyl ester (90 mg, 0.14 mmol, 31%).

NMR (CDCl$_3$, δ (ppm)); 0.04 (12H, s), 0.86 (24H), 1.1~1.7 (13H, m), 2.1~2.7 (10H, m), 3.63 (3H, s), 3.8~4.3 (2H, m), 5.35~5.60 (2H, m).

IR (liquid film, cm$^{-1}$); 2970, 2950, 2870, 1720, 1460, 1435, 1405, 1370, 1360, 1250, 1155, 1100, 1000, 970, 935, 880, 835, 805, 770, 730.

$[\alpha]_D^{20}$ −35.5° (c 1.02, CH$_3$OH).

MS (20 eV; m/e, %); 581 (8, M-t-C$_4$H$_9$), 506 (4), 449 (30), 431 (10), 417 (8), 407 (18), 339 (10), 321 (9), 297 (8), 143 (12), 111 (11), 75 (100).

(iv) 17(S),20-dimethyl-6-oxoprostaglandin $E_1$ Methyl Ester

In a similar way to preceding (ii), 11,15-bis(t-butyldimethylsilyl)-17(S),20-dimethyl-6-oxoprostaglandin $E_1$ methyl ester (90 mg, 0.14 mmol) was dissolved in acetonitrile (10 ml), to which pyridine (0.25 ml) and then hydrogen bluoridepyridine (0.5 ml) were added and the mixture was allowed to react at room temperature for 3 hours. After the reaction solution was neutralized with an aqueous saturated solution of sodium hydrogencarbonate, it was extracted with ethyl acetate and the separated organic layer was washed with a saturated saline solution, dried over magnesium sulfate, and concentrated under reduced pressure to give 80 mg of a crude product. This crude product was subjected to preparative thin-layer chromatography (hexane:ethyl acetate =1:4) to obtain 17(S),20-dimethyl-6-oxoprostaglandin $E_1$ methyl ester (45 mg, 0.12 mmol, 86%).

NMR (CDCl$_3$, δ (ppm)); 0.86 (6H), 1.0~1.7 (12H, m), 2.1~2.7 (10H, m), 3.3 (1H, disappeared by D$_2$O), 3.60 (3H, s), 3.8~4.3 (3H, reduced to 2H by D$_2$O), 5.4~5.6 (2H, m).

IR (liquid film, cm$^{-1}$); 3420, 2950, 2920, 2870, 1740, 1720, 1460, 1440, 1415, 1380, 1290, 1250, 1200, 1160, 1980, 1010, 970.

$[\alpha]_D^{25}$ −44.9° (c 0.44, CH$_3$OH).

MS (20 eV; m/e, %); 392 (12, M-H$_2$O), 374 (22), 293 (18), 261 (15), 243 (17), 233 (18), 231 (37), 215 (25), 187 (18), 179 (22), 143 (100), 133 (23), 127 (40), 111 (74), 57 (34).

(v) The following compounds were prepared in the same way as (i) (a), (ii) or (iii).

17(R),20-dimethyl-6-oxoprostaglandin $E_1$ methyl ester (v-1)

15-cyclopentyl-ω-pentanor-6-oxoprostaglandin $E_1$ methyl ester (v-2)

15-cyclohexyl-ω-pentanor-6-oxoprostaglandin $E_1$ methyl ester (v-3)

16-cyclohexyl-ω-tetranor-6-oxoprostaglandin $E_1$ methyl ester (v-4)

18-oxa-6-oxoprostaglandin $E_1$ methyl ester (V-5)

16-methyl-6-oxoprostaglandin E₁ methyl ester (v-6)
16,16-dimethyl-6-oxoprostaglandin E₁ methyl ester (v-7)
15-methyl-6-oxoprostaglandin E₁ methyl ester (v-8)
17,17-dimethyl-6-oxoprostaglandin E₁ methyl ester (v-9)

The spectra of the respective compounds are compiled in Table 5 below.

TABLE 5

| Example | NMR (CDCl₃, δ (ppm)) | IR (liquid film, cm⁻¹) | MS (m/e) |
|---|---|---|---|
| v - 1 | 0.86 (6H), 1.0~1.7 (13H, m), 2.1~2.7 (10H, m), 3.3 (1H), 3.60 (3H, s), 3.8~4.3 (3H), 5.4~5.6 (2H, m). | 3420, 1740, 1720, 1380, 1160, 1080, 970. | 392 (M—H₂O) 374 (M—2H₂O). |
| v - 2 | 0.9~3.1 (25H, m), 3.60 (3H, s), 3.8~4.3 (2H, m), 5.45~5.65 (2H, m). | 3400, 1740, 1720, 1370, 1160, 970. | 362 (M—H₂O), 344 (M—2H₂O). |
| v - 3 | 0.9~3.1 (27H, m), 3.63 (2H, s), 3.8~4.3 (2H, m) 5.4~5.6 (2H, m). | 3420, 1740, 1720, 1375, 1160, 970. | 376 (M—H₂O) 358 (M—2H₂O). |
| v - 4 | 0.9~3.1 (29H, m), 3.63 (3H, s), 3.8~4.3 (2H, m), 5.4~5.6 (2H, m). | 3420, 1740, 1720, 1375, 1160, 970. | 390 (M—H₂O), 372 (M—2H₂O). |
| v - 5 | 1.17 (3H, t, J = 7 Hz), 1.0~1.9 (6H, m), 2.1~2.7 (12H, m), 3.25~3.67 (4H, m), 3.60 (3H, s), 3.8~4.3 (2H, m), 5.55~5.75 (2H, m). | 3400, 1740, 1720, 1375, 1170, 970. | 366 (M—H₂O) 348 (M—2H₂O). |
| v - 6 | 0.87 (6H), 1.0~1.7 (11H, m), 2.1~2.7 (12H, m), 3.63 (3H, s), 3.8~4.3 (2H, m), 5.4~5.6 (2H, m). | 3420, 1750, 1720, 1380, 1160, 1080, 970. | 378 (M—H₂O) 360 (M—2H₂O). |
| v - 7 | 0.87 (9H), 1.0~1.7 (10H, m), 2.1~2.7 (12H, m), 3.63 (3H, s), 3.8~4.3 (2H, m), 5.45~5.65 (2H, m). | 3420, 1740, 1720, 1380, 1160, 1080, 970. | 392 (M—H₂O) 374 (M—2H₂O). |
| v - 8 | 0.87 (6H), 1.0~1.7 (12H, m), 2.1~3.1 (12H, m), 3.60 (3H, s), 3.8~4.3 (1H, m), 5.4~5.6 (2H, m). | 3400, 1740, 1720, 1380, 1160, 1080, 970. | 378 (M—H₂O), 360 (M—H₂O). |
| v - 9 | 0.87 (9HO, 1.0~1.7 (10H, m), 2.1~2.7 (12H, m), 3.63 (3H, s), 3.8~4.3 (2H, m), 5.4~5.6 (2H, m). | 3420, 1740, 1720, 1380, 1160, 1080, 970. | 392 (M—H₂O), 374 (M—2H₂O). |

(vi) 11,15-bis(t-butyldimethylsilyl)-6-oxoprostaglandin F₁α and F₁β methyl ester A methanol solution (1.6 ml, 0.82 mmol) of 2.8% sodium methylate was added to a methanol solution (10 ml) of a mixture of 11,15-bis(t-butyldimethylsilyl)-6-nitroprostaglandin F₁α and F₁β methyl ester, and the mixture was stirred at room temperature for 5 minutes. The resulting solution was added to the mixture of an aqueous solution (10 ml) of ammonium acetate (7.7 g, 0.1 mol and an aqueous solution (10.2 ml, 16.4 mmol) of 25% titanium trichloride, and the mixture was stirred at room temperature for 18 hours.

The reaction mixture was neutralized by an aqueous solution of sodium hydrogencarbonate, extracted three times with ethyl acetate (100 ml). The organid layer was washed with an aqueous solution of sodium chloride, dried over magnesium sulfate, and concentrated to give a residue (497 mg). The residue was chromatographed on a silica gel column using hexane-ethylacetate (3:1–1:2) as an elvent to give 11,15-bis(t-butyldimethylsilyl)-6-oxoprostaglandin F₁α methylester (257 mg, 0.42 mmol, 61%) and 11,15-bis(t-butyldimethylsilyl)-6-oxoprostaglandin F₁β methyl ester (138 mg, 0.23 mmol, 33%).

11,15-bis(t-butyldimethylsilyl)-6-oxoprostaglandin F₁α methyl ester:

NMR (CDCl₃, δ (ppm)); 0.04 (12H, s), 0.86 (21H), 1.0~2.8 (23H, m), 3.60 (3H, s), 3.65~4.25 (3H, m), 5.25~5.45 (2H, m).

IR (liquid film, cm⁻¹); 3460, 2950, 2870, 1740, 1720, 1460, 1360, 1250, 1060, 1000, 970, 835, 775.

Mass (20 eV; m/e, %); 594 (M-H₂O, 10), 555 (M-ᵗBu, 34), 538 (41), 463 (27), 423 (31), 405 (46), 391 (58), 379 (40), 331 (33), 267 (97), 215 (75), 175 (72), 143 (100), 111 (56), 75 (42), 73 (47).

11,15-bis(t-butyldimethylsilyl)-6-oxoprostaglandin F₁β methyl ester:

NMR (CDCl₃, δ (ppm)); 0.06 (12H, s), 0.87 (21H), 1.0~2.8 (22H, m), 3.61 (2H, s), 3.75~4.35 (4H, m), 5.2~5.4 (2H, m).

IR (liquid film, cm⁻¹); 3500, 2950, 2870, 1740, 1710, 1460, 1360, 1250, 1060, 1000, 970, 835, 775.

Mass (20 eV; m/e, %); 594 (M-H₂O, 2), 555 (3), 538 (4), 506 (23), 488 (31), 413 (27), 395 (35), 267 (16), 241 (15), 215 (32), 201 (12), 175 (29), 143 (45), 115 (11), 111 (25), 75 (100).

(vii) 6-oxoprostaglandin F₁α methyl ester

The 11,15-bis(t-butyldimethylsilyl)-6-oxoprostaglandin F₁α methyl ester (124 mg, 0.203 mmol) obtained in Example (VI) was dissolved in acetonitrile (10 ml). 0.25 ml of pyridine and 0.5 ml of hydrogen fluoride-pyridine were added to the solution and the mixture was stirred at room temperature for 1 hour. The reaction mixture was neutralized by use of an a aqueous solution of sodium hydrogencarbonate, extracted four times with ethyl acetate (50 ml), washed with an aqueous solution of sodium shloride, dried over magnesium sulfate, and concentrated to obtained 85 mg of a crude product. This product was separated by column chromatography (ethyl acetate:acetone=4:1) on silica gel to obtain 6-oxoprostaglandin F₁α methylester (65 mg, 0.169 mmol, 83%).

NMR (CDCl₃, δ (ppm)); 0.87 (3H, t), 1.0~1.8 (16H, m), 2.1~2.7 (6H, m), 3.2~4.3 (6H, m), 3.61 (3H, s), 5.2~5.6 (2H, m).

IR (liquid film, cm⁻¹); 3400, 2950, 2870, 1710, 1430, 1240, 1190, 1175, 1040, 965.

Mass (20 eV; m/e, %); 366 (M-H₂O, 13), 348 (M-2H₂O, 18), 335 (8), 330 (5), 323 (14), 319 (12), 279 (23), 265 (33), 223 (67), 208 (39), 196 (72), 195 (54), 164 (34), 143 (96), 121 (43), 111 (83), 99 (100), 95 (58), 71 (27).

6-oxoprostaglandin F₁β was obtained from the 11,15-bis(t-butyldimethylsilyl)-6-oxoprostaglandin F₁β methyl ester according to the same method.

NMR (CDCl₃, δ (ppm)); 0.87 (3H, t), 1.1~2.7 (22H, m), 3.0~4.2 (6H, m), 3.62 (3H, s), 5.3~5.55 (2H, m).

IR(CHCl₃, cm⁻¹); 3300, 2930, 2870, 1710, 1440, 1260, 1170, 1040, 960.

Mass (20 eV ; m/e , %); 366 (M-H$_2$O, 2), 348 (M-2H$_2$O, 8), 330 (3), 190 (16), 157 (14), 143 (100), 136 (44), 129 (13), 117 (13), 115 (14), 111 (80), 109 (13), 99 (28).

(viii) 6-oxoprostaglandin F$_1\alpha$:

A methanol solution (1 ml) of 6-oxoprostaglandin F$_1\alpha$ methyl ester (26 mg, 60 μmol) was dissolved in an aqueous solution (0.14 ml, 0.68 mmol) of 5N sodium hydroxide, and the mixture was stirred at room temperature for 3 hours. To the reaction mixture a saturated aqueous solution of ammonium chloride, and the reaction mixture was neutralized with an aqueous solution of hydrochloric acid, and extracted five times with ethyl acetate (50 ml). The organic layer was washed with an aqueous solution of sodium chloride, dried over magnesium sulfate, and concentrated to obtain 25 mg of a crude product. This product was purified by colum chromatography (ethyl acetate:acetone:acetio acid=90:10:1) on silica gel to obtaine 6-oxoprostaglandin F$_1\alpha$ (21 mg, 57 μmol, 84%). The spectral data of this compound coincided with those of authentic sample.

Rf: 0.28 (chloroform:methanol:acetic acid=90:5:5, yellow spot shown with anisaldehyde-sulfuric acid reagent at room temperature)

(B) Preparation of 6-oxoprostaglandin E$_1$ derivatives from 4-substituted-2-cyclopentenone (i) dl-11,15-bis(t-butyldimethylsilyl)-6-oxoprostaglandin E$_1$ methyl ester and its 15-epimer A pentane solution of 2.0 M t-butyllithium (2.6 ml, 5.2 mmol) was added to an ether solution (30 ml) of dl-(E)-3-t-butyldimethylsilyloxy-1-iodo-1-octene (957 mg, 26 mmol) at $-78°$ C. and the mixture was stirred for 1 hour. An ether solution (10 ml) of cuprous iodide (495 mg, 2.6 mmol) and tributylphosphine (1.05 g, 5.2 mmol) was added to the reaction solution and the mixture was stirred at $-78°$ C. for 30 minutes. An either solution (10 ml) of dl-4-t-butyldimethylsilyloxy-2-cyclopentenone (424 mg, 2.0 mmol) was added to the above solution and the admixture was stirred at $-78°$ C. for 5 minutes and then at $-40°$ C. for additional 15 minutes.

Further, an ether solution (10 ml) of methyl 6-nitro-6-heptenoate (374 mg, 2.0 mmol) was added to the reaction system and stirred at $-40°$ C. for 30 minutes. Furthermore, an aqueous solution prepared by dissolving ammonium acetate (6 g, 78 mmol) and an aqueous solution of titanium trichloride (25%, 8 ml, about 13 mmol) in water (20 ml), and tetrahydrofuran (100 ml) was added thereto and was stirred at room temperature for 12 hours. The reaction mixture was neutrized by an aqueous solution of sodium hydrogencarbonate, extracted with ethyl acetate (100 ml×3). The separated organic layer was washed with a saturated saline solution, dried over magnesium sulfate, and concentrated under reduced pressure to give 2.97 g of a crude product. This crude product was subjected to column chromatography on silica gel (hexane:ethyl acetate=19:1) to obtain a mixture (516 mg, 0.846 mmol, 42%) of dl-11,15-bis(t-butyldimethylsilyl)-6-oxoprostaglandin E$_1$ methyl ester and its 15-epimer. The spectrum data of the compound perfectly coincided with those obtained in (A), (i), (a).

(b) In the same way as the preceding (a), dl-(E)-3-t-butyldimethylsilyloxy-1-iodo-1-octene, dl-4-t-butyldimethylsilyloxy-2-cyclopentenone, and methyl 6-nitro-6-heptenoate were allowed to react. Then 10 ml of 1 normal hydrochloric acid and tetrahydrofuran (100 ml) were added thereto and the mixture was stirred at 40° C. for 18 hours. Thereafter, the reaction solution was put to the same work-up as (a) to give 2.80 g of a crude product, which was then separated by column chromatography on silica gel to obtain a mixture (408 mg, 0.668 mmol, 34%) of dl-11,15-bis(t-butyldimethylsilyl)-6-oxoprostaglandin E$_1$ methyl ester and its 15-epimer.

(ii) 6-oxoprostaglandin E$_1$ methyl ester

According to the same method as (a), (3S)-(E)3-t-butyldimethylsilyloxy-1-iodo-1-octene (957 mg, 2.6 mmol; $[\alpha]_D^{21}$ $-30.6°$ (c 1.57, CCl$_2$)0 and (4R)-4-t-butyldimethylsilyloxy-2-cyclopentenone (424 mg, 20 mmol ; $[\alpha]_D^{22}$ $+63.2°$ (c 1.04, CH$_3$OH)) were allowed to react and then methyl 6-nitro-6-heptenoate (374 mg, 2.0 mmol) was allowed to react therewith. Furthermore, an aqueous solution prepared by dissolving ammonium acetate (6 g, 78 mmol) and an aqueous solution of 25% titanium trichloride (8 ml, about 13 mmol) in water (20 ml) and methanol (70 ml) was added to the resulting reaction solution and the admixture was stirred at room temperature for 15 hours. After a saturated aqueous solution of sodium hydrogencarbonate was added to the reaction solution, the reaction solution was extracted with ether and the separated organic layer was washed with a saturated saline solution, dried over magnesium sulfate, and concentrated under reduced pressure to give 2.70 g of a crude product. Chromatographic separation of the crude product was carried out on a column of silica gel (Wako gel C-300, 100 g; hexane:ethyl acetate =19:1) to obtain 11,15-bis(t-butyldimethylsilyl)-6-oxoprostaglandin E$_1$ methyl ester (634 mg, 1.038 mmol, 52%). NMR, IR, MS, and TLC of this compound perfectly coincided with those of the dl compound of (A), (i), (a).

The above-mentioned 11,15-bis(t-butyldimethylsilyl)-6-oxoprostaglandin E$_1$ methyl ester (68 mg, 0.11 mmol) was dissolved in 10 ml of acetonitrile, to which 0.25 ml of pyridine and then 0.5 ml of hydrogen fluoride-pyridine were added and the reaction was conducted at room temperature for 3 hours. After the reaction solution was neutralized with an saturated aqueous solution of sodium hydrogencarbonate, it was extracted with ethyl acetate and the separated organic layer was washed with a saturated saline solution, dried over magnesium sulfate, and concentrated under reduced pressure to give 60 mg of a crude product. Separation was effected by subjecting the crude product to preparative thin-layer chromatography (hexane : ethyl acetate=1:4, developed twice) to obtain 6-oxoprostaglandin E$_1$ methyl ester (31 mg, 0.081 mmol, 74%).

The spectrum data of this compound coincided with those obtained in (A), (ii).

(iii) 11,15-bis(t-butyldimethylsilyl)-17(S), 20-dimethyl-6-oxoprostaglandin E$_1$ methyl ester In the same way as (i), (a), (3S, 5S)-(E)-3-t-butyldimethylsilyloxy-1-iso-5-methyl-1-nonene (1.29 g, 3.25 mmol; $[\alpha]_D^{23}$ $-36.5°$ (c 0.63, CH$_3$OH)) was first allowed to react with (4R)-4-t-butyldimethylsilyloxy-2-cyclopentenone (530 mg, 2.5 mmol; $[\alpha]_D^{22}$ $+63.2°$ (c 1.04, CH$_3$OH)) and then with methyl 6-nitro-6-heptenoate (468 mg, 2.5 mmol). Then an aqueous solution prepared by dissolving ammonium acetate (6.94 g, 90 mmol) and an aqueous solution of 25% titanium trichloride (9.3 ml, about 15 mmol) in 23 ml of water, and tetrahydrofuran (115 ml) were added to the obtained reaction solution and the mixture was stirred at room temperature for 18 hours. After the reaction was completed, the reaction product was subjected to work-up according to (ii) and was chromatographed on a column of silica gel hexane:ethyl acetate=9:1) to obtain 11,15-bis(t-butyldimethylsilyl)-17(S),20-dimethyl-6-oxoprostaglandin $E_1$ methyl ester (832 mg, 1.30 mmol, 52%).

The spectrum data of this compound coincided with those obtained in (A), (iii).

(iv) 17(S),20-dimethyl-6-oxoprostaglandin $E_1$ methyl ester

In the same way as (ii), 11,15-bis(t-butyldimethylsilyl)-17(S),20-dimethyl-6-oxoprostaglandin $E_1$ methyl ester (250 mg, 0.39 mmol) was dissolved in acetonitrile (18 ml). Firstly pyridine (0.45) and then hydrogen fluoride-pyridine (0.9 ml) were added to the above solution and the reaction was conducted at room temperature for 1 hour and twenty minutes. The reaction solution was subjected to the same work-up as (ii) to give 210 mg of a crude product. The crude product was separated by preparative thin-layer chromatography (hexane:ethyl acetate=1:4) to obtain 17(S), 20-dimethyl-6-oxoprostaglandin $E_1$ methyl ester (131 mg, 0.32 mmol, 82%). The spectrum data of this compound coincided with those obtained in (A), (iv).

(v) The following compounds were prepared according to the same methods as (i), (ii), and (iii).

17(R), 20-dimethyl-6-oxoprostaglandin $E_1$ methyl ester
15-cyclopentyl-ω-pentanor-6-oxoprostaglandin $E_1$ methyl ester
15-cyclohexyl-ω-pentanor-6-oxoprostaglandin $E_1$ methyl ester
16-cyclohexyl-ω-tetranor-6-oxoprostaglandin $E_1$ methyl ester
18-oxa-6-oxoprostaglandin $E_1$ methyl ester
16-methyl-6-oxoprostaglandin $E_1$ methyl ester
16,16-dimethyl-6-oxoprostaglandin $E_1$ methyl ester
15-methyl-6-oxoprostaglandin $E_1$ methyl ester
17,17-dimethyl-6-oxoprostaglandin $E_1$ methyl ester The spectrum data of the above-mentioned compounds coincided respectively with those obtained in (A), (v).

EXAMPLE 19~22

A mixture (91%) of 11,15-bis(t-butyldimethylsilyl)-6-nitro-2,3-dinorprostaglandin $F_1\alpha$ methyl ester and $F_1\beta$ methyl ester was prepared from 11,15-bis(t-butyldimethylsilyl)-6-nitro-2,3-dinorprostaglandin $E_1$ methyl ester obtained in Example 10 according to the same method as the reduction in Example 9 (Example 19).

11,15-bis(t-butyldimethylsilyl)-6-oxo-2,3-dinorprostaglandin $F_1\alpha$ methyl ester (52%) was obtained according to the same method as Example 18-(A)-(vi) (Example 20).

6-oxo-2,3-dinorprostaglandin $F_1\alpha$ methyl ester (87%) was obtained according to the same method as Example 18-(A)-(vii) (Example 21).

6-oxo-2,3-dinorprostaglandin $F_1\alpha$ (79%) was obtained according to the same method as Example 18-(A)-(viii) (Example 22).

The spectral data of these compounds are shown in Table 6.

TABLE 6

| Example | NMR (CDCl$_3$, δ (ppm)) | IR (liquid film, cm$^{-1}$) | Mass (m/e) |
| --- | --- | --- | --- |
| 19 | 0.06 (12H, 8), 0.85 (21H), 1.1~2.4 (19H, m), 3.60 (3H, s), 3.8~4.2 (3H, m), ~4.8 (1H, b), 5.2 5.45 (2H, m). | 3500, 2950, 2860, 1735, 1550, 1460, 1435, 1360, 1250, 1060, 1000, 965, 835, 770. | 558 (M—57), 544, 527, 466, 435. |
| 20 | 0.06 (12H, s), 0.87 (21H), 1.0~2.8 (19H, m), 3.60 (3H, s), 3.65~4.25 (3H, m), 5.25~5.45 (2H, m). | 3480, 2950, 2870, 1740, 1720, 1460, 1360, 1250, 1060, 1000, 970, 835, 775. | 566 (M—H$_2$O), 527 (M—57), 510, 435, 395. |
| 21 | 0.87(3H, t), 1.0~1.8 (12H, m), 2.1~2.7 (6H, m), 3.2~4.3 (6H, m), 3.60 (3H, s) 5.2~5.6 (2H, m). | 3400, 2950, 2870, 1710, 1430, 1240, 1190, 1175, 1040, 965. | 338 (M—H$_2$O), 320 (M—2H$_2$O), 307, 302 (M—3H$_2$O). |
| 22 | | 3000, 1700. | |

EXAMPLE 23

Preparation of prostaglandin $E_1$ derivatives from 6-nitroprostaglandin $E_1$ derivatives (i) dl-15(RS)-11,15-bis(t-butyldimethylsilyl) prostaglandin $E_1$ methyl ester dl-15(RS)-11,15-bis(t-butyldimethylsilyl)-6-nitroprostaglandin $E_1$ methyl ester (57 mg, 0.089 mmol) was dissolved in 3 ml of toluene, and tributyltin hydride (104 mg, 0.356 mmol, 3 eq) and α,α'-azobisisobutyronitrile (7.3 mg, 0.045 mmol) were added thereto and the mixture was heated under reflux for two hours. After the mixture was cooled, it was chromatographed on a column of silica gel and eluted with benzene. The eluted benzene solution was concentrated to give 32 mg of a crude product. The crude product was subjected to preparative thin-layer chromatography (hexane:ethyl acetate=6:1) to obtain dl-15(RS)-11,15-bis (t-butyldimethylsilyl) prostaglandin $E_1$ methyl ester (20 mg, 0.034 mmol, 38%). The above-mentioned compound accorded with the authentic sample obtained separately in thin-layer chromatography (3-solvent system), NMR, IR, and Mass.

NMR (CDcl$_3$, δ (ppm)); 0.07 (12H, s), 0.89 (18H, s), 0.90 (3H, m), 1.1~3.0 (24H, m), 3.70 (3H, s), 3.7~4.4 (2H, m), 5.4~5.7 (2H, m)

IR (liquid film, cm$^{-1}$); 2960, 2950, 2870, 1740, 1460, 1430, 1360, 1250, 1160, 1115, 1100, 1000, 965, 879, 835, 770.

Mass (20 eV; m/e, %); 581 (M-με, 0.3), 565 (M-oμe, 0.4), 539 (M-tβu, 24), 536 (10), 504 (4), 464 (4), 408 (23), 407 (73), 393 (26), 376 (20), 375 (62), 301 (27), 215 (10), 75 (100).

(ii) 11,15-bis(t-butyldimethylsilyl)prostaglandin $E_1$ methyl ester

Tributyltin hydride (290 mg, 1 mmol, 5 eq) was added to 11,15-bis(t-butyldimethylsilyl)-6-nitroprostaglandin $E_1$ methyl ester (127 mg, 0.198 mmol), to which mixture α,α'-azobisisobutyronitrile was added little by little and the mixture was allowed to react at 110° C. for 1.5 hours. After the reaction solution was cooled, it was subjected to column chromatography on silica gel to give 86 mg of a crude product. The crude product was subjected to preparative thin-layer chromatography (hexane:ethyl acetate=6:1) to obtain 11,15-bis(t-butyldimethylsilyl)prostaglandin $E_1$ methyl ester (30 mg, 0.050 mmol, 25%). The spectrum data of this compound perfectly coincided with those of the authentic sample.

Thus obtained compound was dissolved in acetonitrile (1 ml) which contained 5% hydrofluoric acid (47%) and the solution was allowed to react at room temperature for 30 minutes to give prostaglandin $E_1$ (14 mg, 0.039 mmol, 78%). This compound accorded perfectly with the authentic sample in spectra.

(iii) Various types of prostaglandin $E_1$ derivatives

Approximately in the same way as Example 23 (i) or (ii), various types of 6-nitro compounds were heated under reflux over 3 to 10 equivalents of tributyltin hydride in toluene to obtain corresponding reductively denitrated compounds (yields 39 to 58%). The 6-nitro compounds were 11,15-bis(t-butyldimethylsilyl)-16,17,18,19,20-pentanor-15-cyclohexyl-6-nitroprostaglandin $E_1$ methyl ester, 11,15-bis(t-butyldimethylsilyl)-16,17,18,19,20-pentanor-15-cyclopentyl-6-nitroprostaglandin $E_1$ methyl ester, 11,15-bis(t-butyldimethylsilyl)-17(S),20-dimethyl-6-nitroprostaglandin $E_1$ methyl ester, 11,15-bis(t-butyldimethylsilyl)-17(R),20-dimethyl-6-nitroprostaglandin $E_1$ methyl ester, and 11,15-bis(t-butyldimethylsilyl)-17,18,19,20-tetranor-16-cyclohexyl-6-nitroprostaglandin $E_1$ methyl ester and they gave respectively corresponding reductively denitrated compounds of prostaglandin $E_1$ derivatives. The various spectrum data of these compounds coincided with those of respective samples.

What we claim is:

1. A 6-nitroprostaglandin derivative of the following formula (I)

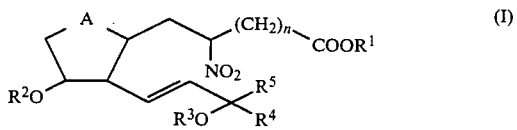

wherein A represents a carbonyl group or a hydroxymethylene group; n represents an integer of 1 to 4; $R^1$ represents a hydrogen atom, a $C_1$–$C_{10}$ alkyl group, a substituted or unsubstituted phenyl group, a substituted or unsubstituted $C_5$–$C_8$ alicyclic group, a substituted or unsubstituted phenyl ($C_1$–$C_2$) alkyl group, or one equivalent of a cation; $R^2$ and $R^3$ are identical or different and each represents a hydrogen atom, a tri($C_1$–$C_7$) hydrocarbon-silyl group, or a group forming an acetal linkage together with the oxygen atom of the hydroxyl group; $R^4$ represents a hydrogen atom, a methyl group, an ethyl group, a vinyl group, or an ethynyl group; $R^5$ represents an unsubstituted $C_5$–$C_8$ alkyl group, a substituted $C_1$–$C_5$ alkyl group substituted by a substituent selected from the group consisting of substituted or unsubstituted phenyl, a substituted or unsubstituted phenoxy and a substituted or unsubstituted $C_5$–$C_6$ cycloalkyl, or a substituted or unsubstituted $C_5$–$C_8$ alicyclic group, and the substiutents of said substituted phenyl, $C_5$–$C_8$ alicyclic and phenyl ($C_1$–$C_2$) alkyl group of $R^1$ and of said substituted phenyl, substituted phenoxy, substituted $C_5$–$C_6$ cyclolkyl and substituted $C_5$–$C_8$ alicyclic group of $R^5$ are selected from the group consisting of a halogen atom, a hydroxyl group, a $C_2$–$C_7$ acyloxy group, a $C_1$–$C_4$ alkyl group, a $C_1$–$C_4$ alkyl group substituted by a halogen atom, a $C_1$–$C_4$ alkoxy group, a $C_1$–$C_4$ alkoxy group substituted by a halogen atom, a nitrile group, a carboxyl group and a ($C_1$–$C_6$) alkoxy-carbonyl group.

2. The 6-nitroprostaglandin derivative of claim 1 which is a compound of the following formula (1)-a

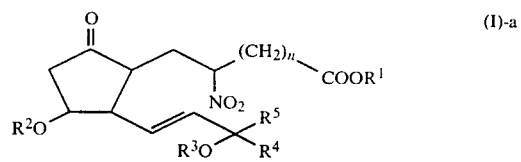

wherein n, $R^1$, $R^2$, $R^3$, $R^4$ and $R^5$ are as defined in claim 1.

3. The 6-nitroprostaglandin derivative of claim 1 which is a compound of the following formula (I)-b

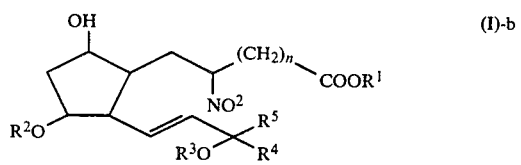

wherein n, $R^1$, $R^2$, $R^3$, $R^4$ and $R^5$ are as defined in claim 1.

4. The 6-nitroprostaglandin derivative of any one of claims 1 to 3 wherein $R^1$ represents a hydrogen atom, a $C_1$–$C_{10}$ alkyl group, or one equivalent of a cation.

5. The 6-nitroprostaglandin derivative of any one of claims 1 to 3 wherein $R^2$ and $R^3$ are identical or different and each represents a hydrogen atom, a tri($C_1$–$C_4$)alkylsiyl group, a diphenyl($C_1$–$C_4$)alkylsilyl group, a 2-tetrahydropyranyl group, a 2-tetrahydrofuranyl group, a 1-ethoxyethyl group, a 2-methoxy-2-propyl group, a (2-methoxyethoxy)methyl group, or a 6,6-dimethyl-3-oxa-2-oxo-dicyclo[3.1.0]hex-4-yl group.

6. The 6-nitroprostaglandin derivative of any one of claims 1 to 3 wherein $R^4$ represents a hydrogen atom or a methyl group.

7. The 6-nitroprostaglandin derivative of any one of claims 1 to 3 wherein $R^5$ represents an n-pentyl, n-hexyl, 2-methyl-1-hexyl, 2-methyl-2-hexyl, cyclopentyl or cyclohexyl group.

8. The 6-nitroprostaglandin derivative of claim 1 which is a 6-nitroprostaglandin derivative of the following formula (I)-a-1 or (I)-b-1:

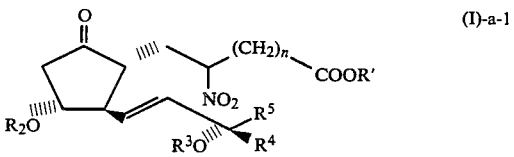

wherein all of the symbols are defined as in formula (I),

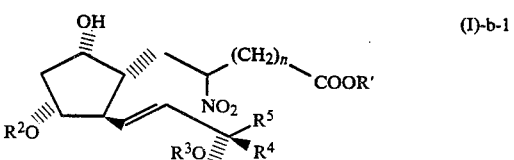

wherein all of the symbols are defined as in formula (I).

9. A pharmaceutical composition for controlling vascular action comprising (1) as an active ingredient a 6-nitroprostaglandin derivative of the following formula (I)-1

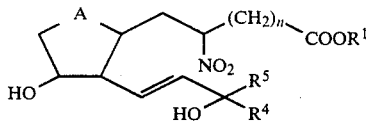

wherein A, n, $R^1$, $R^4$ and $R^5$ are as defined with regard to formula (I) of claim 1, and (2) a pharmaceutically acceptable carrier.

10. The pharmaceutical composition of claim 9 wherein the active ingredient is a 6-nitroprostaglandin $E_1$ derivative of the following formula (I)-a-1

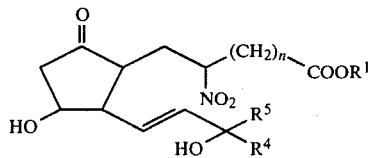

wherein n, $R^1$, $R^4$ and $R^5$ are as defined with regard to formula (I).

11. A medicament in unit dosage form comprising the pharmaceutical composition of claim 9 or 10.

12. A method for controlling the vascular actions of a warm-blooded animal which comprises administering a pharmaceutically effective amount of the compound of formula (I)-1 or formula (I)-a-1 either as such, or as the pharmaceutical composition of claim 16 or 10 respectively or as the medicament of claim 11 to a warm-blooded animal which requires such control.

13. The method of claim 12 wherein the warm-blooded animal is a human being.

14. The method of claim 12 wherein the pharmaceutically effective amount is about 0.01 μg to about 20 mg/kg of body weight per day.

* * * * *